(12) United States Patent
Chang et al.

(10) Patent No.: US 7,037,681 B2
(45) Date of Patent: May 2, 2006

(54) PLASMODIUM FALCIPARUM MEROZOITE SURFACE PROTEIN-1 MALARIA PRODUCED IN TRANSGENIC PLANTS

(75) Inventors: Sandra P. Chang, Honolulu, HI (US); David A. Christopher, Honolulu, HI (US); Benjamin Vine, Honolulu, HI (US); Wei-Wen Su, Honolulu, HI (US); Robert Bugos, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 210 days.

(21) Appl. No.: 10/098,514

(22) Filed: Mar. 11, 2002

(65) Prior Publication Data

US 2002/0194648 A1 Dec. 19, 2002

Related U.S. Application Data

(63) Continuation-in-part of application No. 09/500,376, filed on Feb. 8, 2000, now Pat. No. 6,855,316.

(60) Provisional application No. 60/274,599, filed on Mar. 9, 2001.

(51) Int. Cl.
*C12P 21/06* (2006.01)
*C07H 21/02* (2006.01)
*C07H 21/04* (2006.01)
*A01H 1/00* (2006.01)

(52) U.S. Cl. .................... 435/69.1; 536/23.1; 536/23.5; 800/278

(58) Field of Classification Search ............... 435/69.1; 536/23.1, 23.5; 800/200, 278
See application file for complete search history.

(56) References Cited

U.S. PATENT DOCUMENTS

| 4,745,051 A | 5/1988 | Smith et al. |
| 6,270,800 B1 | 8/2001 | Speaker et al. |
| 6,297,428 B1 * | 10/2001 | Guilley et al. ............... 800/280 |
| 6,420,523 B1 | 7/2002 | Chang et al. |

FOREIGN PATENT DOCUMENTS

EP 0 329 257 8/1989

OTHER PUBLICATIONS

ANNON. "Human Clinical Trials of Plant Engineered as Vaccine are Successful; May Usher in New Era for Plant/Pharmaceutical Research," Am. Soc. Plant Phys. Newsletter 25(3):9 (1998).
Bevan M., "Binary Agrobacterium vectors for plant transformation." Nucleic Acids Res. Nov. 26, 1984;12(22): 8711-21.
Burghaus Pa, et al., "Immunization of Aotus nancymai with recombinant C terminus of *Plasmodium falciparum* merozoite surface protein 1 in lipsomes and alum adjuvant does not induce protection against a challenge infection." Infect Immun. 1996 Sep.;64(9):3614-9.
Chang SP, et al., "A carboxyl-terminal fragment of *Plasmodium falciparum* gp195 expressed by a recombinant baculovirus induces antibodies that completely inhibit parasite growth." J Immunol. Jul. 15, 1992;149(2):548-55.
Chang SP, et al., "Generalized immunological recognition of the major merozite surface antigen (gp195) of *Plasmodium falciparum*." Proc Natl Acad Sci U S A. Aug. 1989;86(16): 6343-7.
Chang SP, et al., "A recombinant baculovirus 42-kilodalton C-terminal fragment of *Plasmodium falciparum* merozoite surface protein 1 protects *Aotus* monkeys against malaria." Infect Immun. Jan. 1996;64(1):253-61.
Cheung et al. "Immunization with synthetic peptides of a *Plasmodium falciparum* surface antigen induces antimerozoite antibodies," Proc. Natl. Acad. Sci. USA 83: 8328 (1986).
Datla, RSS, et al., "Improved high-level constitutive foreign gene expression in plants using an AMV RNA4 untranslated leader sequence," Plant Science 94(1/2):139 1993.
Ellis, R.W., "New Technologies for Making Vaccines," in Vaccines, Plotkin, S.A. and Mortimer, Jr. E.A., eds., W.B. Saunders Co., Philadelphia (1988), Ch. 29, pp. 568-575.
Estruch, J.J. et al., "Transgenic plants: an emerging approach to pest control." Nat Biotechnol. Feb. 1997;15(2): 137-41.
Fisher, DE and Guiltinan, MJ, "Rapid, Efficient Production of Homozygous Transgenic Tobacco Plaints with *Agrobacterium tumefaciens*: A Seed-to-Seed Protocol," Plant Mol. Biol. Reporter 13(3):278-289 (1995).

(Continued)

Primary Examiner—Mark Navarro
(74) Attorney, Agent, or Firm—Todd A. Lorenz; Dorsey & Whitney LLP

(57) ABSTRACT

This invention is in the field of recombinant *Plasmodium falciparum* polypeptides and relates to recombinant or synthetic antigen compositions which comprise p42 antigens, and more specifically to methods and compositions for the expression of *Plasmodium falciparum* polypeptides in transgenic plants.

15 Claims, 11 Drawing Sheets

OTHER PUBLICATIONS

Fraley RT, et al., "Expression of bacterial genes in plant cells." Proc Natl Acad Sci U S A. Aug. 1983;80(15):4803-7.

Fromm, H. et al., "An octopine synthase enhancer element directs tissue-specific expression and binds ASF-1, a factor from tobacco nuclear extracts." Plant Cell. Oct. 1989;1(10):977-84.

Gallie DR, et al., "The 5'-leader sequence of tobacco mosaic virus RNA enhances the expression of foreign gene transcripts in vitro and in vivo." Nucleic Acids Res. Apr. 24, 1987; 15(8):3257-73.

Gomord V, et al., "The C-terminal HDEL sequence is sufficient for retention of secretory proteins in the endoplasmic reticulum (ER) but promotes vacuolar targeting of proteins that escape the ER." Plant J. Feb. 1997;11(2):313-25.

Hall et al. "Major surface antigen gene of a human malaria parasite cloned and expressed in bacteria," Nature 311:379 (1984).

Hasegawa A, et al., "The complete sequence of soybean chlorotic mottle virus DNA and the identification of a novel promoter." Nucleic Acids Res. Dec. 11, 1989;17(23):9993-10013.

Haseloff J, et al., "Removal of a cryptic intron and subcellular localization of green fluorescent protein are required to mark transgenic Arabidopsis plants brightly." Proc Natl Acad Sci U S A. Mar. 18, 1997;94(6):2122-7.

Haq TA, et al., "Oral immunization with a recombinant bacterial antigen produced in transgenic plants." Science. May 5, 1995;268(5211):714-6.

Helliwell CA, and Gray JC. "The sequence surrounding the translation initiation codon of the pea plastocyanin gene increases translational efficiency of a reporter gene." Plant Mol Biol. Nov. 1995;29(3):621-6.

Herrera et al. "Conserved Polypeptides of *Plasmodium falciparum* as Malaria Vaccine Candidates?", Acta Leidensia, 60(1):107-110 (1991).

Herrera et al. "Immunization of *Aotus* monkeys with *Plasmodium falciparum* blood-stage recombinant proteins," Proc. Natl. Acad. Sci. USA 87:4017 (1990).

Holder et al, "Immunization against blood-stage rodent malaria using purified parasite antigens," Nature 294:361 (1981).

Holder et al., "A hybrid gene to express protein epitopes from both sporozoite and merozoite surface antigens of *Plasmodium falciparum*," Parasitology, 97:373-382 (1988).

Holder, A.A. et al., "Immunization against *Plasmodium falciparum* with recombinant polypeptides produced in *Escherichia coli*," Parasite Immunology, 10(6):607-617 (1988).

Holder et al., "Primary Structure of the Precursor to the three major surface antigens of *Plasmodium falciparum* merozoite," Nature, 317:270-273 (1985).

Holder et al., "Processing of the precursor to the major merozoite surface antigens of *Plasmodium falciparum*," Parasilogy, 94:199-208 (1987).

Hui et al. "Serum from Pf195 protected *Aotus* Monkeys Inhibit *Plasmodium falciparum* growth in Vitro," Exp. Parasitol. 64:519 (1987).

Iannacone, R. et al., "Specific sequence modifications of a cry3B endotoxin gene result in high levels of expression and insect resistance." Plant Mol Biol. Jun. 1997;34(3):485-96.

Jobling SA, and Gehrke L, "Enhanced translation of chimaeric messenger RNAs containing a plant viral untranslated leader sequence." Nature. Feb. 12-18, 1987; 325(6105):622-5.

Joshi RL, et al. "BSMV genome mediated expression of a foreign gene in dicot and monocol plant cells." EMBO J. Sep. 1990;9(9):2663-9.

Knapp, B. et al. "A histidin alanine rich recombinant antigen protects *aotus* monkeys from P. Falciparium infection," Behring Inst. Mitt. 82:349-59 (1988).

Koziel MG, et al., "A cauliflower mosaic virus promoter directs expression of kanamycin resistance in morphogenic transformed plant cells." J Mol Appl Genet. 1984;2(6):549-62.

Kumar S, et al., "Immunogenicity and efficacy in *aotus* monkeys of four recombinant *Plasmodium falciparum* vaccines in multiple adjuvant formulations based on the 19-kilodalton C terminus of merozoite surface protein 1" Infect Immun. Apr. 2000;68(4):2215-23.

Lew et al. "A protective monoclonal antibody recognizes a linear epitope in the precursor to the major merozoite antigens of *Plasmodium chabaudi adami*," Proc. Natl. Acad. Sci. USA 86:3768 (1989).

Locher CP, et al., "*Plasmodium falciparum*: gp195 tripeptide repeat-specific monoclonal antibody inhibits parasite growth in vitro." Exp Parasitol. Oct. 1996;84(1):74-83.

Lumbreras, V. et al., "The use of an alternative promoter in the *Arabidopsis thaliana* HMG1 gene generates an mRNA the encodes a novel 3-hydroxy-3-methylglutaryl coenzyme A reductase isoform with an extended N-terminal region." Plant J. Oct. 1995;8(4):541-9.

Ma JK, et al., "Generation and assembly of secretory antibodies in plants." Science. May 5, 1995; 268(5211):716-9.

Maiti IB, and Shepherd RJ. "Isolation and expression analysis of peanut chlorotic streak caulimovirus (PCISV) full-length transcript (FLt) promoter in transgenic plants." Biochem Biophys Res Commun. Mar. 17, 1998;244(2):440-4. Errata appears in Biochem Biophys Res Commun. Jul. 9, 1998;248(1):210.

Mason HS, et al., "Expression of hepatitis B surface antigen in transgenic plants." Proc Natl Acad Sci U S A. Dec. 15, 1992;89(24):11745-9.

Mitra A, et al., "A Chiorella virus gene promoter functions as a strong promoter both in plants and bacteria." Biochem Biophys Res Commun. Oct. 14, 1994;204(1):187-94.

Majarian et al., "Passive Immunization against Murine Malaria with an IgG3 Monoclonal Antibody," J. Immunol. 132:3131 (1984).

Moffat AS. "Exploring transgenic plants as a new vaccine source," Science. May 5, 1995;268(5211):658-660.

Murphy, V.F. et al., "Expression of hybrid malaria anitgens in insect cells and their engineering for correct folding and secretion," Parasitology, 100 pt. 2:177-183 (1990).

Odink K.G. et al., "Expression of cloned cDNA for a major surface antigen of *Plasmodium falciparum* merozoite," FEBS Lett. (1984) 108-12.2

Ohme-Takagi, M. et al., "The effect of sequences with high AU content on mRNA stability in tobacco." Proc Natl Acad Sci U S A. Dec. 15, 1993; 90(24):11811-5.

Patarroyo et al. "A synthetic vaccine protects humans against challenge with asexual blood stages of *Plasmodium falciparum* malaria," Nature 332:158 (1988).

Patarroyo et al. "Induction of protective immunity against experimental infection with malaria using synthetic peptides," Nature 328:629 (1987).

Patarroyo et al. "Protective Synthetic Peptides against Experimental *Plasmodium falciparum*-Induced Malaria," Vaccines 87 (Brown, Chanock, Lerner, ed.) Cold Spring Harbor Laboratory Press, Cold Spring Harbor, NY. 117-124 (1987).

Perrin et al. "Antimalarial Immunity in Saimiri Monkeys," J. Exp. Med. 160:441 (1984).

Potter, RH and Jones, MGK, Plant Gene Transfer, in Plant and Molecular Biology, A Laboratory Manual, Clark, M. S. (ed.)Springer, chap. 8, pp. 400-426 (1997).

Rodriguez et al. "Studies In Owl Monkeys Leading to the Development of a Synthetic Vaccine Against the Asexual Blood Stages of *Plasmodium Falciparum*," Am. J. Trop. Med. Hyg. 43:339 (1990).

Ruebush et al., "Immunization of Owl Monkeys with a Combination of *Plasmodium Falciparum* Asexual Blood-Stage Synthetic Peptide Antigens," Am. J. Trop. Med. Hyg. 43:355-366 (1990).

Sanger M, et al., "Characteristics of a strong promoter from figwort mosaic virus: comparison with the analogous 35S promoter from cauliflower mosaid virus and the regulated mannopine synthase promoter," Plant Mol Biol. Mar. 1990; 14(3):422-43.

Saul et al., Second African Malaria Vaccine Testing Network Meeting, Accra, Ghana, Nov. 24-26, 1997.

Schwarz et al, "Structural Diversity of the Major Surface Antigen of *Plasmodium falciparum* Merozoites," Mol. Cell. Biol., 6(3):964-968 (1986).

Shirsat, A. et al., "Sequences responsible for the tissue specific promoter activity of a pea legumin gene in tobacco." Mol Gen Genet. Jan. 1989;215(2):326-31.

Siddiqui et al. "Merozoite surface coat precursor protein completely protects *Aotus* monkeys against *Plasmodium falciparum* malaria," 1987. Proc. Natl. Acad. Sci. USA 84:3014.

Sijmons PC, et al., "Production of correctly processed human serum albumin in transgenic plants." Biotechnology (N Y). Mar. 1990;8(3):217-21.

Smilek, D. et al., "A single amino acid change in myelin basic protein peptide confers the capacity to prevent rather than induce EAE", Proc. Natl. Acad. Sci. USA 88:9633-37 (1991).

Soltysik, "Structure/function studies of QS-21 adjuvant; assessment of triterpene aldehyde and glucuronic acid rules in adjuvant function," Vaccine 1995, 13(15):1403-1410.

Staub, JM et al., "High-yield production of a human therapeutic protein in tobacco chloroplast," Nat. Biotech. 18:333-338 (2000).

Stowers AW, et al., "A recombinant vaccine expressed in the milk of transgenic mice protects *Aotus* monkeys from a lethal challenge with *Plasmodium falciparum*." Proc Natl Acad Sci U S A. Jan. 8, 2002;99(1):339-44. Epub Dec. 18, 2001.

Stowers AW, et al., "Efficacy of two alternate vaccines based on *Plasmodium falciparum* merozoite surface protein 1 in an *Aotus* challenge trial." Infect Immun. Mar. 2001;69(3):1536-46.

Tanabe, K. et al. "Alletic Dimorphism in a Surface Antigen Gene of the Malaria Parasite *Plasmodium falciparum*," J. Mol. Biol., 195:273-287 (1987).

Tian, Y.C. et al., "Insect resistance of transgenic tobacco plants expressing delta-endotoxin gene of *Bacillus thuringiensis*." Chin J Biotechnol. 1991;7(1):1-13.

Turpen TH, et al., "Malarial epitopes expressed on the surface of recombinant tobacco mosaic virus." Biotechnology (N Y). Jan. 1995;13(1):53-7.

* cited by examiner

Fig. 7(A)

MSP1.p42 FUP

401 AAAATGATATTAAAT TTGCACAGGA AGGTATAAG TTATTATGAAAAGGTT

601 AACATTGAGAC CTTATACAATAAC TTAGTTAATAAAAT TGACGATTACTT

951 TCCAGAAAAT TCTGGATGTTTCAGAC ATTTAGATGAAAG AGAAGAATGTA

MSP1.p42FVO

181 AATTTCAAAATG TTTTAGAATCAGATTTA ATTCCATATAAAG ATTTA

230 ACATCAAGTAATT ATGTTGTCAAAGATCCA TATAAATTTCTTAATAAA

277 GAAAAAGAGA TAAATTCTTAAGCAGTTA TAATTATATTAAGGATTC

Fig. 7(B)

```
  A   E   F   D   N   I   L   S   D   N   I   L   S   G   F   E   N   E      18
GCC GAA TTC GAC AAC ATC CTC AGT GAC AAC ATC CTC AGT GGC TTC GAG AAC GAG      54

Y   D   V   I   Y   L   K   P   L   A   G   V   Y   R   S   L   K   K      36
TAC GAC GTA ATC TAC CTA AAG CCC CTT GCC GGT GTC TAC CGT TCA TTG AAG AAA     108

Q   I   E   K   N   I   F   T   F   N   L   N   L   N   D   I   L   N      54
CAG ATA GAA AAG AAT ATT TTC ACG TTC AAC CTC AAC CTA AAT GAC ATC CTC AAC     162

S   R   L   K   K   R   K   Y   F   L   D   V   L   E   S   D   L   M      72
TCG CGC CTC AAG AAG CGA AAA TAC TTC CTC GAC GTG TTG GAA TCC GAC CTT ATG     216

Q   F   K   H   I   S   S   N   E   Y   I   I   E   D   S   F   K   L      90
CAA TTC AAG CAC ATT AGC TCT AAC GAG TAC ATC ATA GAG GAC AGC TTC AAG CTC     270

L   N   S   E   Q   K   N   T   L   L   K   S   Y   K   Y   I   K   E     108
TTG AAT TCA GAA CAG AAG AAC ACC CTC CTA AAG TCC TAC AAA TAC ATT AAG GAG     324

S   V   E   N   D   I   K   F   A   Q   E   G   I   S   Y   Y   E   K     126
TCT GTT GAG AAC GAC ATC AAG TTC GCC CAG GAA GGA ATT AGC TAC TAT GAG AAA     378

V   L   A   K   Y   K   D   D   L   E   S   I   K   K   V   I   K   E     144
GTC CTG GCT AAA TAC AAG GAC GAC TTG GAA AGC ATT AAG AAG GTA ATC AAA GAA     432

E   K   E   K   F   P   S   S   P   P   T   T   P   P   S   P   A   K     162
GAG AAG GAA AAG TTT CCG AGC TCT CCA CCC ACA ACT CCC CCA TCG CCT GCA AAG     486

T   D   E   Q   K   K   E   S   K   F   L   P   F   L   T   N   I   E     180
ACC GAC GAG CAG AAA AAA GAA AGT AAG TTC CTT CCA TTC CTC ACC AAC ATC GAA     540

T   L   Y   N   N   L   V   N   K   I   D   D   Y   L   I   N   L   K     198
ACT CTA TAT AAC AAC CTG GTG AAC AAG ATT GAT GAC TAC TTA ATC AAC TTG AAG     594

A   K   I   N   D   C   N   V   E   K   D   E   A   H   V   K   I   T     216
GCG AAA ATT AAT GAC TGT AAC GTC GAA AAG GAT GAA GCC CAC GTT AAG ATC ACC     648

K   L   S   D   L   K   A   I   D   D   K   I   D   L   F   K   N   H     234
AAG CTT TCC GAT CTC AAA GCC ATC GAC GAT AAG ATT GAC CTG TTT AAG AAC CAC     702

N   D   F   D   A   I   K   K   L   I   N   D   D   T   K   K   D   M     252
AAC GAT TTC GAC GCA ATC AAA AAG TTG ATC AAC GAC GAT ACT AAG AAA GAC ATG     756

L   G   K   L   L   S   T   G   L   V   Q   N   F   P   N   T   I   I     270
CTT GGA AAA CTG CTG TCG ACA GGC TTG GTC CAA AAC TTC CCG AAC ACC ATT ATA     810

S   K   L   I   E   G   K   F   Q   D   M   L   N   I   S   Q   H   Q     288
AGC AAG CTG ATC GAA GGA AAG TTT CAG GAT ATG CTG AAC ATC TCT CAG CAT CAA     864

C   V   K   K   Q   C   P   E   N   S   G   C   F   R   H   L   D   E     306
TGC GTG AAG AAG CAA TGT CCC GAG AAT TCA GGT TGC TTC CGC CAC TTA GAC GAA     918

R   E   E   C   K   C   L   L   N   Y   K   Q   E   G   D   K   C   V     324
AGG GAG GAA TGT AAA TGC CTG CTG AAT TAT AAA CAG GAA GGA GAC AAG TGC GTA     972

E   N   P   N   P   T   C   N   E   N   N   G   G   C   D   A   D   A     342
GAG AAT CCT AAC CCA ACC TGT AAC GAA AAT AAC GGT GGC TGC GAT GCT GAC GCT    1026

K   C   T   E   E   D   S   G   S   N   G   K   K   I   T   C   E   C     360
AAG TGT ACC GAG GAG GAC AGC GGT TCC AAT GGC AAG AAA ATA ACT TGC GAA TGC    1080

T   K   P   D   S   Y   P   L   F   D   G   I   F   C   S   H   D   E     378
ACG AAG CCC GAT AGT TAC CCT CTC TTC GAC GGT ATC TTC TGC TCC CAT GAT GAG    1134

L   *   E   L   T                                                         383
CTT TAA GAG CTC ACC
```

Fig. 8

```
  R   I   Q   G   D   I   T   M   D   N   I   L   S   G   F   E   N   E    18
CGG ATC CAA GGA GAT ATA ACA ATG GAC AAC ATC CTC AGT GGC TTC GAG AAC GAG      54

Y   D   V   I   Y   L   K   P   L   A   G   V   Y   R   S   L   K   K    36
TAC GAC GTA ATC TAC CTA AAG CCC CTT GCC GGT GTC TAC CGT TCA TTG AAG AAA     108

Q   I   E   K   N   I   F   T   F   N   L   N   L   N   D   I   L   N    54
CAG ATA GAA AAG AAT ATT TTC ACG TTC AAC CTC AAC CTA AAT GAC ATC CTC AAC     162

S   R   L   K   K   R   K   Y   F   L   D   V   L   E   S   D   L   M    72
TCG CGC CTC AAG AAG CGA AAA TAC TTC CTC GAC GTG TTG GAA TCC GAC CTT ATG     216

Q   F   K   H   I   S   S   N   E   Y   I   I   E   D   S   F   K   L    90
CAA TTC AAG CAC ATT AGC TCT AAC GAG TAC ATC ATA GAG GAC AGC TTC AAG CTC     270

L   N   S   E   Q   K   N   T   L   L   K   S   Y   K   Y   I   K   E   108
TTG AAT TCA GAA CAG AAG AAC ACC CTC CTA AAG TCC TAC AAA TAC ATT AAG GAG     324

S   V   E   N   D   I   K   F   A   Q   E   G   I   S   Y   Y   E   K   126
TCT GTT GAG AAC GAC ATC AAG TTC GCC CAG GAA GGA ATT AGC TAC TAT GAG AAA     378

V   L   A   K   Y   K   D   D   L   E   S   I   K   K   V   I   K   E   144
GTC CTG GCT AAA TAC AAG GAC GAC TTG GAA AGC ATT AAG AAG GTA ATC AAA GAA     432

E   K   E   K   F   P   S   S   P   P   T   T   P   P   S   P   A   K   162
GAG AAG GAA AAG TTT CCG AGC TCT CCA CCC ACA ACT CCC CCA TCG CCT GCA AAG     486

T   D   E   Q   K   K   E   S   K   F   L   P   F   L   T   N   I   E   180
ACC GAC GAG CAG AAA AAA GAA AGT AAG TTC CTT CCA TTC CTC ACC AAC ATC GAA     540

T   L   Y   N   N   L   V   N   K   I   D   D   Y   L   I   N   L   K   198
ACT CTA TAT AAC AAC CTG GTG AAC AAG ATT GAT GAC TAC TTA ATC AAC TTG AAG     594

A   K   I   N   D   C   N   V   E   K   D   E   A   H   V   K   I   T   216
GCG AAA ATT AAT GAC TGT AAC GTC GAA AAG GAT GAA GCC CAC GTT AAG ATC ACC     648

K   L   S   D   L   K   A   I   D   D   K   I   D   L   F   K   N   H   234
AAG CTT TCC GAT CTC AAA GCC ATC GAC GAT AAG ATT GAC CTG TTT AAG AAC CAC     702

N   D   F   D   A   I   K   K   L   I   N   D   D   T   K   K   D   M   252
AAC GAT TTC GAC GCA ATC AAA AAG TTG ATC AAC GAC GAT ACT AAG AAA GAC ATG     756

L   G   K   L   L   S   T   G   L   V   Q   N   F   P   N   T   I   I   270
CTT GGA AAA CTG CTG TCG ACA GGC TTG GTC CAA AAC TTC CCG AAC ACC ATT ATA     810

S   K   L   I   E   G   K   F   Q   D   M   L   N   I   S   Q   H   Q   288
AGC AAG CTG ATC GAA GGA AAG TTT CAG GAT ATG CTG AAC ATC TCT CAG CAT CAA     864

C   V   K   K   Q   C   P   E   N   S   G   C   F   R   H   L   D   E   306
TGC GTG AAG AAG CAA TGT CCC GAG AAT TCA GGT TGC TTC CGC CAC TTA GAC GAA     918

R   E   E   C   K   C   L   L   N   Y   K   Q   E   G   D   K   C   V   324
AGG GAG GAA TGT AAA TGC CTG CTG AAT TAT AAA CAG GAA GGA GAC AAG TGC GTA     972

E   N   P   N   P   T   C   N   E   N   N   G   G   C   D   A   D   A   342
GAG AAT CCT AAC CCA ACC TGT AAC GAA AAT AAC GGT GGC TGC GAT GCT GAC GCT    1026

K   C   T   E   E   D   S   G   S   N   G   K   K   I   T   C   E   C   360
AAG TGT ACC GAG GAG GAC AGC GGT TCC AAT GGC AAG AAA ATA ACT TGC GAA TGC    1080

T   K   P   D   S   Y   P   L   F   D   G   I   F   C   S   H   D   E   378
ACG AAG CCC GAT AGT TAC CCT CTC TTC GAC GGT ATC TTC TGC TCC CAT GAT GAG    1134

L   *   E   L   T                                                        383
CTT TAA GAG CTC ACC                                                       1149
```

DNA AND AMINO ACID SEQUENCE OF BVp42-M attggatccactaaa

```
 13 atgtggtcttggaagtgtcttttattctgggctgtcttggtgacc
     M  W  S  W  K  C  L  F  W  A  V  L  V  T
 58 gccactctttgcacagcagcgatctctgttactatggacaacatc
     A  T  L  C  T  A  A  I  S  V  T  M  D  N  I
103 ctcagtggcttcgagaacgagtacgacgtaatctacctaaagccc
     L  S  G  F  E  N  E  Y  D  V  I  Y  L  K  P
148 cttgccggtgtctaccgttcattgaagaaacagatagaaaagaat
     L  A  G  V  Y  R  S  L  K  K  Q  I  E  K  N
193 attttcacgttcaacctcaacctaaatgacatcctcaactcgcgc
     I  F  T  F  N  L  N  L  N  D  I  L  N  S  R
238 ctcaagaagcgaaaatacttcctcgacgtgttggaatccgacctt
     L  K  K  R  K  Y  F  L  D  V  L  E  S  D  L
283 atgcaatttaagcacattagctctaacgagtacatcatagaggac
     M  Q  F  K  H  I  S  S  N  E  Y  I  I  E  D
328 agcttcaagctcttgaattcagaacagaagaacaccctcctaaag
     S  F  K  L  L  N  S  E  Q  K  N  T  L  L  K
373 tcctacaaatacattaaggagtctgttgagaacgacatcaagttc
     S  Y  K  Y  I  K  E  S  V  E  N  D  I  K  F
418 gcccaggaaggaattagctactatgagaaagtcctggctaaatac
     A  Q  E  G  I  S  Y  Y  E  K  V  L  A  K  Y
463 aaggacgacttggaaagcattaagaaggtaatcaaagaagagaag
     K  D  D  L  E  S  I  K  K  V  I  K  E  E  K
508 gaaaagtttccgagctctccacccacaactcccccatcgcctgca
     E  K  F  P  S  S  P  P  T  T  P  P  S  P  A
553 aagaccgacgagcagaaaaagaaagtaagttccttccattcctc
     K  T  D  E  Q  K  K  E  S  K  F  L  P  F  L
598 accaacatcgaaactctatataacaacctggtgaacaagattgat
     T  N  I  E  T  L  Y  N  N  L  V  N  K  I  D
643 gactacttaatcaacttgaaggcgaaaattaatgactgtaacgtc
     D  Y  L  I  N  L  K  A  K  I  N  D  C  N  V
688 gaaaaggatgaagcccacgttaagatcaccaagcttccgatctc
     E  K  D  E  A  H  V  K  I  T  K  L  S  D  L
733 aaagccatcgacgataagattgacctgtttaagaaccacaacgat
     K  A  I  D  D  K  I  D  L  F  K  N  H  N  D
778 ttcgacgcaatcaaaaagttgatcaacgacgatactaagaaagac
     F  D  A  I  K  K  L  I  N  D  D  T  K  K  D
823 atgcttggaaaactgctgtcgacaggcttggtccaaaacttcccg
     M  L  G  K  L  L  S  T  G  L  V  Q  N  F  P
868 aacaccattataagcaagctgatcgaaggaaagtttcaggatatg
```

Fig. 10 (continue)

```
         N  T  I  I  S  K  L  I  E  G  K  F  Q  D  M
913  ctgaacatctctcagcatcaatgcgtgaagaagcaatgtcccgag
         L  N  I  S  Q  H  Q  C  V  K  K  Q  C  P  E
958  aattcaggttgcttccgccacttagacgaaagggaggaatgtaaa
         N  S  G  C  F  R  H  L  D  R  E  E  C  K
1003 tgcctgctgaattataaacaggaaggagacaagtgcgtagagaat
         C  L  L  N  Y  K  Q  E  G  D  K  C  V  E  N
1048 cctaacccaacctgtaacgaaaataacggtggctgcgatgctgac
         P  N  P  T  C  N  E  N  N  G  G  C  D  A  D
1093 gctaagtgtaccgaggaggacagcggttccaatggcaagaaaata
         A  K  C  T  E  E  D  S  G  S  N  G  K  K  I
1138 acttgcgaatgcacgaagcccgatagttaccctctcttcgacggt
         T  C  E  C  T  K  P  D  S  Y  P  L  F  D  G
1183 atcttctgctcc
         I  F  C  S ccacctcatcatcatcatcatcattaataaggtaccta
 P  P  H  H  H  H  H  *  *
```

PLASMODIUM FALCIPARUM MEROZOITE SURFACE PROTEIN-1 MALARIA PRODUCED IN TRANSGENIC PLANTS

This application claims priority to U.S. Provisional Application Ser. No. 60/274,599, filed Mar. 9, 2001; and is a continuation-in-part of U.S. patent application Ser. No. 09/500,376, filed Feb. 8, 2000 now U.S. Pat. No. 6,855,316.

FIELD OF THE INVENTION

This invention is in the field of recombinant *Plasmodium falciparum* polypeptides and relates to recombinant or synthetic antigen compositions comprising p42 antigens, and more specifically to methods and compositions for expressing *Plasmodium falciparum* polypeptides in transgenic plants.

BACKGROUND OF THE INVENTION

The major merozoite surface protein of Plasmodium species has been shown to be a target of varying degrees of protective immunity against the asexual blood stages in rodent and human malaria. For example, vaccination of mice with purified P230, the major merozoite surface protein of the rodent malaria *Plasmodium yoelii*, has resulted in reduced parasitemias in comparison to controls upon intravenous challenge with a lethal dose of parasitized erythrocytes (Holder et al. (1981) *Nature* 294:361). Mice have also been protected against *P. yoelii* by passive transfer of a monoclonal antibody (Mab) specific for P230 (Majarian et al. (1984) *J. Immunol.* 132:3131) and against (rodent malaria) *Plasmodium chabaudi adami* challenge by passive immunization with a Mab specific for the homologous 250-kDa molecule of this plasmodium species (Lew et al. (1989) *Proc. Natl. Acad. Sci. USA* 86:3768). The ability to confer resistance to parasite challenge by passive transfer of antibodies suggests that antibody-mediated mechanisms play an important role in antigen-specific immunity to malaria.

Despite these findings, however, no commercially viable vaccine has been developed against the major merozoite surface antigen of the major human malaria pathogen, *Plasmodium falciparum*. For example, using naturally derived materials, such as the precursor of the major merozoite surface protein (MSP) alone (gp195: 195,000–200,000 Da molecular species; merozoite surface protein-1 (MSP-1)), gp195 mixed with certain of its natural processing fragments, or a natural processing fragment by itself, partial protection against *Plasmodium falciparum* infection was achieved by some researchers (Hall et al. (1984) *Nature* 311:379; Perrin et al. (1984) *J. Exp. Med.* 160:441; Patarroyo et al. (1987) *Vaccines* 87 (Brown, Chanock, Lerner, ed.) Cold Spring Harbor Laboratory Press, CSH, N.Y. 117–124). An effective vaccine against *Plasmodium falciparum* cannot convey merely partial protection, however, since even low parasitemias of this organism can cause serious illness. A commercially useful vaccine should substantially eliminate parasitemia.

More recently, attention has been focused on the 42 kDa C-terminal processing fragment of gp-195 (p42). See Chang et al. (1996) *Infect Immun* 64(1):253. Co-pending U.S. patent application Ser. No. 08/195,705, the disclosure of which is incorporated by reference herein, describes a p42 peptide composition produced in a baculovirus vector and expressed in insect host cells. Similarly, co-pending U.S. patent application Ser. No. 09/500,376, the disclosure of which is incorporated by reference herein, describes a modified p42 peptide composition in combination with an adjuvant, wherein the p42 polypeptide is also produced in a baculovirus vector and expressed in insect host cells. "BVp42" as used herein refers to the expression of p42 in insect cells as described in these patents. Although capable of providing an immunogenic p42 polypeptide, the above-described methods may be cost prohibitive for commercial feasibility, particularly for a therapeutic agent primarily targeted to third world developing countries.

What is needed, therefore, is a method of producing an immunogenic p42 polypeptide which can reduce the costs associated with p42 production while still providing adequate amounts of immunogen. While transgenic plant expression is one potential option, earlier studies have demonstrated the inherent difficulties associated with expression of foreign (or non-plant) proteins in plant host cells. See, e.g., Estruch et al. (1997) *Nat. Biotechnol.* 15(2): 137; Tian et al. (1991) *Chin J Biotechnol.* 7(1):1; Iannacone et al. (1997) *Plant Mol. Biol.* 34(3):485; and Ohme-Takagi et al. (1993) *Proc Natl Acad Sci U.S.A.* 90(24): 11811. Accordingly, a successful method for expressing malarial antigens in transgenic plants will have to overcome these problems.

To date, there has been only one other published study describing the expression of *Plasmodium gene* sequences in plants. In this study, several sequential B-cell epitopes were expressed on the surface of the Tobacco Mosaic Virus, creating plant virus particles which are transiently produced in infected tobacco tissue (Turpen et al. 1995. Biotechnology 13(1):53).

SUMMARY OF THE INVENTION

The present invention solves the aforementioned problems in the prior art through the provision of recombinant malarial antigens and methods for expressing these antigens in transgenic plants. In a preferred embodiment, dicotyledonous plants are infected with *Agrobacterium* strains containing at least one binary vector carrying a modified p42 nucleic acid sequence and an antibiotic resistance plant selectable marker, and at least one other plasmid carrying the vir-region of a tumor-inducing plasmid. In one aspect of the invention, the dicotyledonous plant is a tobacco plant. In a particularly preferred aspect of the invention, the *Agrobacterium* strain is *Agrobacterium tumefaciens* strain LBA4404.

In one embodiment, an isolated p42 nucleic acid encoding a p42 polypeptide is provided, wherein said p42 nucleic acid is preferentially recognized by an *Agrobacterium*-mediated plant expression system thereby resulting in increased translation of the mRNA transcribed from said p42 nucleic acid. In a further embodiment, the sequence of said isolated p42 nucleic acid has been modified to remove potential polyadenylation sequences, cryptic intron splice sites and RNA instability sequences, thereby resulting in enhanced RNA transcription and stability. In an alternative embodiment, the sequence of said isolated p42 nucleic acid has been modified to reduce A:T content in said sequence.

In a preferred embodiment, the invention provides an NtMSP1.42C nucleic acid wherein the codons encoding the upstream signal sequence of said NtMSP1.42S have been substituted by codons encoding a consensus sequence for ribosomal binding and a translation initiation site. In a particularly preferred embodiment, the nucleic acid comprises nucleotide sequences from 1 through about 1149 of SEQ ID NO: 3.

In another embodiment, the invention provides an *Agrobacterium*-mediated plant expression system for the production of p42 polypeptide, comprising a DNA construct consisting of operatively linked DNA coding for a modified T-region but no vir-region, wherein said modified T-region comprises naturally occurring border sequences consisting of about 23 nucleotides at the extremities of said modified T-region and wherein the aforementioned p42 nucleic acid or NtMSP1.42S nucleic acid is flanked by said border sequences. In a further embodiment, the invention provides a dicotyledonous plant comprising the *Agrobacterium*-mediated plant expression system of claim 5. In a preferred embodiment, the dicotyledonous plant comprises a *Nicotiana tabacum* plant. In a still further embodiment, the expression system further comprises a suitable selection marker. In one such embodiment, the selection marker comprises a kanamycin resistance gene.

In another embodiment, the invention provides a method of producing a p42 polypeptide, comprising the steps of: a) introducing an *Agrobacterium* strain into a plant cell wherein said *Agrobacterium* strain comprises at least one plasmid having the vir-region of a tumor-inducing plasmid but having virtually no T-region, and at least one other plasmid comprising the modified T-region of claim 5 but having no vir-region, wherein said plant cell becomes transformed; and b) extracting said p42 polypeptide from said transformed plant cell. In a preferred embodiment, the *Agrobacterium* strain is *Agrobacterium tumefaciens* strain LBA4404. In a further embodiment, the extracted p42 polypeptide obtained by such method comprises amino acid sequences from 1 through about 383 of SEQ ID NO: 2 or amino acids from 1 through about 383 of SEQ ID NO:4.

In another aspect of the present invention, an isolated NtMSP1.42S polypeptide is provided wherein said polypeptide is encoded by a nucleic acid sequence comprising sequences from one 1 through about 1149 of SEQ ID NO: 1. In a preferred embodiment, the isolated NtMSP1.42S polypeptide comprises amino acid sequences from 1 through about 383 of SEQ ID NO: 2. In another embodiment, the invention provides an isolated NtMSP1.42C polypeptide wherein the upstream signal sequence of p42 or NtMSP1.42S polypeptide has been substituted by codons encoding a consensus sequence for ribosomal binding and a translation initiation site. In a preferred embodiment, the isolated polypeptide comprises amino acids from 1 through about 383 of SEQ ID NO:4.

BRIEF DESCRIPTION OF THE DRAWINGS

FIGS. 7A–B show identification of cryptic intron recognition sequences (underlined), polyadenylation signals (bold), and RNA instability sequences "ATTTA" (italics) in (7A) (SEQ ID NO:15) the original MSP1.42 FUP and (7B) (SEQ ID NO:16) FVO DNA sequences.

FIG. 8 shows the nucleotide sequence of the NtMSP1.42S construct modified for optimized transgenic plant expression comprising nucleotides 1–1149 of SEQ ID NO: 1 and its deduced amino acid sequence comprising amino acids 1–383 of SEQ ID NO:2.

FIG. 9 shows the nucleotide sequence of the NtMSP1.42S (SEQ ID NO:1) construct in which the 24 nucleotides encoding the upstream signal sequence have been substituted by 24 consensus nucleotides optimized for transgenic plant translation initiation encoding a consensus sequence for ribosomal binding and a translation initiation site, comprising nucleotides 1–1149 of SEQ ID NO:3 (NtMSP1.42C) and its deduced amino acid sequence comprising amino acids 1–383 of SEQ ID NO:4.

FIG. 10 shows the nucleotide sequence of the p42-M construct modified for optimized insect cell line expression comprising nucleotides 1–1232 of SEQ ID NO:13 and its deduced amino acid sequence comprising amino acids 1–402 of SEQ ID NO:14.

DETAILED DESCRIPTION OF THE INVENTION

The present invention provides compositions and methods for producing an immunogenic p42 polypeptide in transgenic plants. In accordance with the methods of the present invention, key structural elements in known p42 nucleotide sequences are identified as negatively affecting protein expression, and modified p42 sequences are provided to resolve these limitations and enable stable expression of p42 immunogenic polypeptides in transgenic plants. In a preferred embodiment detailed herein, an *Agrobacterium*-mediated binary vector expression system is utilized in a dicotyledonous plant. In a particularly preferred embodiment, the dicotyledonous plant is a tobacco plant.

"NtMSP1.42," as described herein, is a variant of the natural p42 processing fragment of gp195 and additionally is a variant of the BVp42 polypeptides. In particular, the NtMSP1.42 nucleic acids contain codons optimized for *Agrobacterium*-mediated expression of the NtMSP1.42 p42 polypeptides in dicotyledonous plant cells. The term "NtMSP1.42," as used herein, refers to variants of BVp42 modified for expression in dicotyledonous plant host cells and additionally describes the p42 amino acid sequences characteristically produced in dicotyledonous plant cells, and in particular, in *Nicotiana tabacum* cells. NtMSP1.42 polypeptides further comprise secreted BVp42 variant polypeptides, and, alternatively, BVp42 variant polypeptides which are retained within the dicotyledonous plant host cell cytoplasm. More particularly, the term "NtMSP1.42S" refers to BVp42 variants which contain an upstream signal sequence ("promoter") and 3' ER retention signal for directing secretion of the NtMSP1.42S polypeptides outside of the dicotyledonous plant host cell whereas the term "NtMSP1.42C" refers to BVp42 variants which contain a 3' ER retention signal for retention of the NtMSP1.42C polypeptides within the dicotyledonous plant host cell. The amino acid sequences of the p42 polypeptides NtMSP1.42S (SEQ ID NO: 2) and NtMSP1.42C (SEQ ID NO: 4), as well as the nucleic acid sequences encoding the NtMSP1.42S (SEQ ID NO: 1) or NtMSP1.42C (SEQ ID NO: 3) polypeptides, are shown in FIGS. 8 and 9, respectively.

A "p42 polypeptide," as defined herein, is a polypeptide comprising a p4.2 amino acid sequence, including fragments and variants thereof, of the *Plasmodium* major merozoite surface protein gp195. The NtMSP1.42S polypeptide is included within the definition of a p42 polypeptide and comprises a p42 polypeptide encoded by an NtMSP1.42S nucleic acid sequence (see e.g., SEQ ID NO: 1), which differs from the p42 nucleic acids (see e.g., SEQ ID NO:13 of FIG. 10). The "NtMSP1.42S" nucleic acid comprises a nucleic acid sequence in which one or more codons have been substituted with codons encoding the same or similar amino acid such that the NtMSP1.42S mRNA transcript is preferentially recognized by the tRNAs present in a tobacco plant host cell. One NtMSP1.42S amino acid sequence, as set forth in SEQ ID NO:2, differs from the amino acid sequence encoded by the p42 nucleic acid sequence set forth in FIG. 10, by residues at positions 1–8, 376–379, and residues at positions 381–383. The NtMSP1.42C polypeptide is further included within the definition of a p42 polypeptide and comprises a p42 polypeptide encoded by an NtMSP1.42C nucleic acid (see e.g., SEQ ID NO: 3) wherein the upstream signal sequence of NtMSP1.42S has been substituted by 24 consensus nucleotides optimized for transgenic plant translation initiation (Helliwell et al., (1995) Plant Mol. Biol. 29:621) encoding a consensus sequence for ribosomal binding and a translation initiation site (Di Sansebastiano et al. (1998) Plant Journal. 15:449), comprising nucleotides 1–1149 of SEQ ID NO:3 (see e.g., amino acid residues 1–383 of SEQ ID NO: 4).

The NtMSP1.42S nucleic acids (see e.g., nucleotides 1–1149 of SEQ ID NO:1) encoding the p42 and NtMSP1.42S polypeptides as described supra (see e.g., amino acid residues 1–383 of SEQ ID NO:2) are included within the definition of p42 nucleic acids. The NtMSP1.42S nucleic acids differ significantly from other previously described p42 nucleic acids (see, e.g., SEQ ID NO:13 of FIG. 10) by the substitution of one or more codons with codons encoding the same or similar amino acids. One NtMSP1.42S nucleotide sequence, as set forth in SEQ ID NO:1, differs from the nucleotide sequence as set forth in FIG. 10 at nucleotide positions 1–24, 222, 1126–1137, and 1141–1149. The NtMSP1.42S mRNA transcript, transcribed from the NtMSP1.42S nucleotides, is preferentially recognized by the tRNAs present in the tobacco plant host cell expression system. This preferential recognition results in enhanced translation of the NtMSP1.42S transcripts and enhanced production of the NtMSP1.42S polypeptide. The NtMSP1.42C nucleic acids (see, e.g., nucleotides 1–1149 of SEQ ID NO:3) are further included within the definition of p42 nucleic acids and comprise nucleic acids encoding NtMSP1.42C polypeptides (see e.g., amino acid residues 1–383 of SEQ ID NO:4) wherein the 24 nucleotides encoding the upstream signal sequence have been substituted by the 24 consensus nucleotides optimized for transgenic plant translation initiation (Helliwell et al., supra) encoding a consensus sequence for ribosomal binding and a translation initiation site (Di Sansebastiano et al., supra).

Techniques which are known to one skilled in the art for expressing one or more foreign genes in plant host cells can be used to practice the present invention. Methodology for transferring foreign genes from *Agrobacterium tumefaciens* into tobacco plant cells, in which the transferred genes are incorporated into the tobacco plant cell genome, is described, for example, in Fisher et al. (1995) *Plant Molecular Biology Reporter* 13:279, incorporated by reference in its entirety.

Figure 1A:
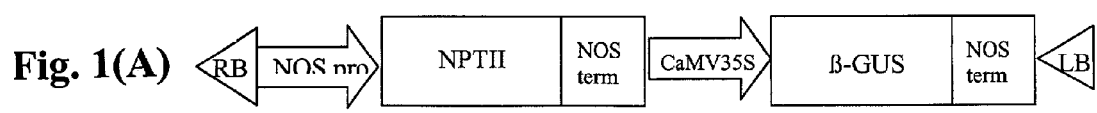
FIGS. 1A–D depict MSP1.42 FUP and MSP1.42 FVO expression constructs based on the pBI121 plant expression vector. (A) pBI121 containing the neomycin phosphotransferase II (NPTII) selectable marker gene encoding kanamycin resistance, the b-glucuronidase gene (b-GUS) under the control of the Cauliflower Mosaic Virus 35S promoter (CaMV35S) and polyadenylation signals from the nopaline synthase gene (NOS term) within the Ti-DNA borders (RB and LB). (B) MSP1.42FUPa construct in which the MSP1.42 FUP gene was inserted into BamHI and SacI sites within the multiple cloning site of pBI121. (C) MSP1.42FUPb construct in which MSP1.42 FUP was inserted into the multiple cloning site of the pBG derivative of pBI121 lacking the b-GUS gene. (D) MSP1.42 FVO constructs in which the 5' region was modified by removal of the flg5 yeast secretion signal present in the original MSP1.42FVO construct and inclusion of a plant translation initiation context sequence (TICS) and ribosome binding site (RBS) (position of these modifications indicated by "a"; MSP1.42FVO-ER has also been modified at the 3' region to fuse the peptide targeting amino acid sequence HDEL to the C terminus (indicated by "b"); alternatively, MSP1.42FVO-His has been modified at the 3' region to fuse a hexa-Histidine sequence to the C terminus (indicated by "c"). Arrows indicate the location of oligonucleotide primers designed to produce these modifications by PCR amplification. 3' region to fuse the peptide targeting amino acid sequence HDEL to the C terminus (indicated by "b"); alternatively, MSP1.42FVO-His has been modified at the 3' region to fuse a hexa-Histidine sequence to the C terminus (indicated by "c"). Arrows indicate the location of oligonucleotide primers designed to produce these modifications by PCR amplification.

In a preferred embodiment, *Agrobacterium* strains are used to mediate the transfer and integration of the NtMSP1.42 nucleotides into tobacco plant chromosomes, using a binary vector strategy. see e.g., Fisher et al., supra; Potter and Jones (1997) Plant Gene Transfer (In Plant Molecular Biology: A Laboratory Manual, M. S. Clark, Ed) Springer-Verlag, Berlin Heidleberg, pp. 397–406; Horsch, et al. (1985) *Science* 227:1229–1231; Klee et al., (1987) *Annual Rev. Plant Physiology* 38:467–486; and Bevan (1984) *Nuc. Acids Res.* 12:8711–8721. According to this strategy, one *Agrobacterium* plasmid contains a vir-region and virtually no T-region and the other, complementary *Agrobacterium* plasmid (the binary vector), carries a modified T-region comprising the NtMSP1.42 nucleotides and an antibiotic resistance plant selectable marker, as described herein.

In another aspect of the invention, the modified T-region of the binary vector further comprising the NtMSP1.42 nucleotides and antibiotic resistance plant selectable marker is flanked by a left and right tumor-inducing plasmid border sequence. The left and right border sequences are defined herein as those sequences located at the left and right extremities of the modified T-region, and flank the respective 5' and 3' ends of the modified T-region. The tumor-inducing plasmid border sequences are required for *Agrobacterium* transfer and integration of the NtMSP1.42 nucleotides and antibiotic resistance plant selectable marker into the chromosomes of host plant cells.

An *Agrobacterium* strain which accomodates both of the described plasmids has the capacity to incorporate the modified T-region of the binary vector comprising the NtMSP1.42 nucleotides and antibiotic resistance plant selectable marker into the chromosomes of dicotyledonous plants such as the tobacco plant.

The NtMSP1.42 nucleotides carried in the binary vector are, in a particularly preferred embodiment, under the control of a Cauliflower Mosaic Virus 35S promoter and nopaline synthase gene terminator.

Other promoters, which are non-constitutive and/or tissue specific, may additionally be used in the invention for improved regulation and/or control of p42 polypeptide expression in specific tissues of the tobacco plant (e.g., leaves, roots, or stems). Such non-constitutive and/or tissue specific promoters include but are not limited to leaf-specific and light-induced promoters such as those from the Lhcb gene (Castresana et al. (1988) *J. European Molecular Biology Organization.* 7:1929–1936), the RbcS gene (Perisic and Lam (1992) *The Plant Cell* 4:831–838.), the psbD gene (Christopher et al. (1992) *The Plant Cell* 4:785–798), sequences from the legA major seed storage gene shown to regulate temporal protein expression (Shirsat et al. (1989) *Mol Gen Genet* 215(2):326), or an alternate promoter in the *Arabidopsis thaliana* HMG1 gene (Lumbreras et al. (1995) *Plant J.,* 8(4):541). New promoters which are specific to plant leaves, roots, or chloroplasts may be isolated by screening genomic libraries to obtain low copy number highly expressed genes. These new promoters can additionally be used in the invention to express p42 polypeptide.

Enhancers which are tissue specific and/or developmentally regulated, may additionally be used in the invention for improved regulation or control of p42 polypeptide expression in specific tissues of the tobacco plant (e.g., leaves, roots, or stems). Such enhancers include but are not limited to, the octopine synthesase enhancer element (Fromm, et al. (1989) *Plant Cell* 1(10):977), as well as other enhancers and enhancer elements which are well known in the art.

The *Agrobacterium* strains of the invention are produced by incorporating, initially into *E. coli,* the NtMSP1.42 nucleotides and antibiotic resistance plant selectable marker into the T-region of a binary vector containing a replicator having a broad host range. The resulting binary vector carrying the modified T-region is subsequently introduced into an *Agrobacterium* strain containing at least one plasmid having a vir-region of a tumor-inducing plasmid and having virtually no T-region. In a preferred embodiment of the invention, the *Agrobacterium* strain is *Agrobacterium tumefaciens* strain LBA4404.

The *Agrobacterium tumefaciens* strain LBA4404 of the invention is a gram-negative bacteria which is the causal agent of crown gall disease in plants. Crown gall disease is characterized by the growth of a gall of dedifferentiated tissues in plants. In this disease, the unregulated growth of plant tissue produces one or more amino acid derivatives, known as opines, which are catabolized by the infecting *Agrobacterium tumefaciens.* Known opines have been classified into three main families whose type members are octapine, nopaline, and agropine. The plant cells comprising the unregulated growing tissues can be grown in culture, and under appropriate conditions, can be regenerated into whole plants which retain certain transformed phentypes.

The *Agrobacterium tumefaciens* of the invention is also a virulent strain of *Agrobacterium* which harbors large plasmids known as tumor-inducing plasmids. The wild-type tumor-inducing plasmids contain regions, known as T-DNA, described supra, which in tumors is integrated into the genome of the host plant. The wild-type T-DNA encodes several transcripts. Mutational studies have shown that some of these transcripts are involved in the induction of tumorous growth. The wild-type T-DNA encodes the gene for at least one opine synthase, and the tumor-inducing plasmids are often classifed by the opine which they express. Each of the wild-type T-DNA genes is under the control of a T-DNA promoter. The T-DNA promoters resemble eukaryotic promoters in structure, and appear to function only in the transformed plant cell. The tumor-inducing plasmid additionally carries genes outside the wild-type T-DNA region. These genes are involved in functions which include opine catabolism, oncogenicity, agrocin sensitivity, replication, and autotransfer to bacterial cells.

If it is desired that the transformed plant cells not be tumorous in character, the oncogenes and other sequences between the left and right tumor-inducing border sequences of the wild-type T-region may be deleted, leaving behind a modified T-region consisting only of the NtMSP1.42 nucleotides, and, if desired, the appropriate antiobiotic resistance plant selectable marker.

Plant cells and plants which are infected by *Agrobacterium tumefaciens* are additionally provided in the invention. The plant cells and plants of the invention include, but are not limited to, cells from dicotyledonous plants as well as whole dicotyledonous plants, such as tobacco, tomato, potato, sugarbeet, sunflower, pea, bean, soybean, and other leguminous plants. The invention also provides cells from monocotyledonous plants as well as whole monocotyledonous plants, such as banana, pineapple, and rice plants. Although, as previously described, several cell types or tissues may be used in the invention, the cells must be totipotent and able to regenerate mature plants.

In a preferred embodiment, the plant tissue and/or plant cells are co-cultivated with *Agrobacterium* for a few days in order to allow transfer of the modified T-DNA comprising the NtMSP1.42 nucleotides and antibiotic resistance plant selectable marker. Subsequent to co-cultivation, the plant cells and tissues are grown on media with an antibiotic which suppresses bacterial growth. The engineered plant cells are able to survive because the antibiotic resistance plant selectable marker is transferred along with the NtMSP1.42 nucleotides. In this manner, the expression system provides for the elimination of all plant cells which are not transformed with the NtMSP1.42 nucleotides.

In a preferred embodiment, the plant cells or plant tissue comprising the leaves of a dicotyledonous plant, such as a tobacco plant, are wounded by any of a number of ways, including but not limited to, cutting with a razor or puncturing with a needle. The exposed dicotyledonous plant tissue is then inoculated with a solution containing an *Agrobacterium* strain containing at least one plasmid having a vir-region of a Ti plasmid and virtually no T-region, and at least one other binary vector having a modified T-region comprising an NtMSP1.42 nucleic acid sequence and an antibiotic resistance plant selectable marker, but containing no vir-region.

In a preferred aspect of the invention, the modified T-region comprises nucleotides 1–1149 of SEQ ID NO: 1 encoding an NtMSP1.42S p42 polypeptide (e.g., SEQ ID NO: 2), and an antibiotic resistance plant selectable marker.

In a further aspect of the invention, the modified T-region comprises nucleotides 1–1149 of SEQ ID NO: 3 encoding an NtMSP1.42C p42 polypeptide (e.g., SEQ ID NO: 4), and an antibiotic resistance plant selectable marker.

In still another embodiment of the invention, the antibiotic resistance plant selectable marker gene comprises a kanamycin resistance gene (e.g., neomycin phosphotransferase II) which provides tobacco plant cell resistance to kanamycin and which further permits the quick selection of regenerated tobacco plants containing the NtMSP1.42S or NtMSP1.42C nucleotides. In a further embodiment of the invention, the kanamycin resistance gene is under the control of a nopaline synthase gene promoter and nopaline synthase gene terminator.

In a preferred embodiment of the invention the NtMSP1.42S or NtMSP1.42C nucleic acid sequences are under the control of a Cauliflower Mosaic Virus 35S promoter and nopaline synthase gene terminator.

In a further aspect of the invention, the NtMSP1.42S or NtMSP1.42C nucleic acid sequences and antibiotic resistance plant selectable marker comprising the modified T-region are flanked by a left and right naturally occurring tumor-inducing border sequence, wherein each left and right border sequence consists of about 23 nucleotides.

In still a further preferred embodiment of the invention, the binary vector carrying the modified T-region is pBIN-mGFP5-ER without mGFP5-ER. In another embodiment of the invention, the binary vector containing the modified T-region is pBI121 without b-GUS.

In an alternate embodiment, other binary vectors containing the modified T-region are used instead of the pBIN-mGFP5-ER without mGFP5-ER or pBI121 without b-GUS binary vector. These binary vectors include, but are not limited to, pBI221 (http://www.clontech.com/techinfo/vectors dis/p35S-GFP.shtml); pBI525 (containing 2 CaMV35S promters, and an enhancer upstream of the multiple cloning site; Datla, et al. (1993) *Plant Science* 94:139–149); pGA or pCIT series vectors (capable of carrying large sequences of foreign DNA); pCG series vectors (highly stable in *Agrobacterium*); pGPTV series vectors (exhibiting a superior capacity for transferring foreign genes into plant host cells); or pBECK2000 series vectors, Binary-BAC vectors, or pGreen series vectors. All of these binary vectors are known in the art and are commonly available.

In a further aspect of the invention, the binary vector carrying the modified T-region is prepared and selected for in *E. coli* strain TOP10F' using a selectable marker which is located on the binary vector in a region outside of the modified T-region.

In a further aspect of the invention, the binary vector containing the modified T-region is transferred by electroporation into an *Agrobacterium* strain containing at least one plasmid having a vir-region of a tumor-inducing plasmid but virtually no T-region.

In a further aspect of the invention, at least one plasmid having a vir-region and virtually no T-region, and at least one other binary vector having a modified T-region comprising the NtMSP1.42S or NtMSP1.42C nucleic acid sequences and an antibiotic resistance plant selectable marker but containing no vir-region, are together transferred into one or more tobacco plant cells upon the inoculation of a dicotyledonous plant, for example a tobacco plant, with a solution which contains the *Agrobacterium*.

In a further aspect of the invention, the modified T-DNA region comprising the NtMSP1.42S or NtMSP1.42C nucleic acid sequences and an antibiotic resistance plant selectable marker, flanked by a left and right tumor-inducing plasmid border sequence, becomes integrated into the genome of one or more dicotyledonous plant host cells, for example, a tobacco plant host cell.

In a further aspect of the invention, the wounded dicotyledonous plant regenerates. In still a further aspect of the invention, the integrated NtMSP1.42S or NtMSP1.42C nucleic acid sequence is expressed as a p42 polypeptide in one or more dicotyledonous plant cells.

In a preferred aspect of the invention, the expressed p42 polypeptide comprises amino acids 1–383 of NtMSP1.42S (SEQ ID NO: 2). In a further aspect of the invention, the expressed polypeptide comprises amino acids 1–383 of NtMSP1.42C (SEQ ID NO: 4).

In still a further aspect of the invention, the p42 polypeptide is harvested from the leaves, roots, or stems of the regenerated dicotyledonous plant.

In a preferred embodiment of the invention, the *Agrobacterium* strain is *Agrobacterium tumefaciens* strain LBA4404

In still another preferred embodiment of the invention, the dicotyledonous plant is a tobacco plant. In an even more preferred embodiment, the tobacco plant is *Nicotiana tabacum cv. xanthi*.

As described herein in the present invention, the p42 "polypeptides" and their grammatical equivalents are proteins, oligopeptides, and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. In some embodiments, for example when the p42 polypeptides are made synthetically, it may be desirable to utilize protein analogs to retard degradation by sample contaminants.

In a preferred embodiment, the p42 polypeptide is isolated. By "isolated polypeptide" herein is meant a polypeptide which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least about 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated p42 polypeptide includes the p42 polypeptide expressed by recombinant cells since at least one component of the polypeptide's natural environment will not be present. Ordinarily, however, isolated p42 polypeptide will be prepared by at least one purification step.

The p42 "extracellular domain" refers to a form of the p42 polypeptide which is essentially free of the transmembrane (Haldar et al. (1985) *J. Biol. Chem.* 260(8):4969–4974) and cytoplasmic domains. Ordinarily, a p42 polypeptide extracellular domain will have less than about 1% of such transmembrane and/or cytoplasmic domains and preferably, will have less than about 0.5% of such domains. It will be understood that any transmembrane domain(s) identified for the p42 polypeptides of the present invention are identified pursuant to criteria routinely employed in the art to identify that type of hydrophobic domain. In a preferred embodiment the transmembrane domain is identified as that portion of the p42 polypeptide that anchors the p42 polypeptide to a membrane. In an alternative embodiment, in the absence of the transmembrane domain (see, e.g., SEQ ID NO: 2), the p42 polypeptide is not anchored to a membrane and is therefore not associated with the cell in which the p42 polypeptide is expressed.

In one embodiment, p42 polypeptides are identified by having substantial amino acid sequence homology with the amino acid sequences provided herein. In another embodiment, p42 polypeptides are identified as being encoded by nucleic acids having substantial nucleic acid sequence homology with the nucleic acid sequences that are provided herein or with the nucleic acid sequences that encode the amino acid sequences provided herein. By "homology" herein is meant sequence similarity and identity with identity being preferred. Such sequence identity or similarity can be based upon the overall amino acid or nucleic acid sequence.

In a preferred embodiment, a polypeptide is a p42 polypeptide as defined herein if the overall sequence identity of the amino acid sequences of FIG. 8 or 9 is preferably greater than about 60%, more preferably greater than about 70%, even more preferably greater than about 80% and most preferably greater than 90%. In some embodiments the sequence identity will be as high as about 93 to 95 or 98%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman (1981) *Adv. Appl. Math.* 2:482, which is expressly incorporated by reference, by the sequence identity alignment algorithm of Needleman & Wunsch (1970) *J. Mol. Biol.* 48:443, which is expressly incorporated by reference, by the search for similarity method of Pearson & Lipman (1988) *Proc. Nat. Acad. Sci. USA* 85:2444, which is expressly incorporated by reference, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984) *Nucl. Acid Res.* 12:387–395, all of which are expressly incorporated by reference, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc., which is expressly incorporated by reference.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351–360; the method is similar to that described by Higgins & Sharp (1989) *CABIOS* 5:151–153, all of which are expressly incorporated by reference. Useful PILEUP parameters include a default gap weight of 3.00, a default gap length weight of 0.10, and weighted end gaps.

Another example of a useful algorithm is the BLAST algorithm, described in Altschul et al., *J. Mol. Biol.* 215, 403–410, (1990) and Karlin et al., *Proc. Nat. Acad. Sci. USA* 90:5873–5787 (1993), all of which are expressly incorporated by reference. A particularly useful BLAST program is the WU-BLAST-2 program which was obtained from Altschul et al., *Methods in Enzymology*, 266: 460–480 (1996); http://blast.wustl/edu/blast/README.html], all of which are expressly incorporated by reference. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucl. Acids Res.* 25:3389–3402, which is expressly incorporated by reference. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of p42 polypeptide. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids or nucleic acid residues than the sequences in the figures, it is understood that in one embodiment, the percentage of sequence identity will be determined based on the number of identical amino acid or nucleic acid residues in relation to the total number of residues. Thus, for example, sequence identity of sequences shorter than that shown in FIG. 8 or 9 as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "longer" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

The p42 polypeptides of the present invention may be shorter or longer than the amino acid sequences shown in the figures. Thus, in a preferred embodiment, included within the definition of p42 polypeptides are portions or fragments of the amino acid sequences provided herein. In one embodiment, fragments of p42 polypeptides are considered p42 polypeptides if a) they share at least one antigenic epitope; b) have at least the indicated sequence identity; and/or c) preferably have p42 polypeptide immunologic activity as defined herein. The nucleic acids encoding the p42 polypeptides also can be shorter or longer than the sequences in the figures.

In addition, as is more fully outlined below, p42 polypeptides can be made that are longer than those depicted in the figures. For example, by the addition of an epitope or purification tags, the addition of other fusion sequences, or the elucidation of additional coding and non-coding sequences. As described below, the fusion of a p42 polypeptide to a polypeptide, such as an upstream leader polypeptide, is particularly preferred.

p42 polypeptides may also be identified as encoded by p42 nucleic acids which hybridize to the sequences depicted in the figures or to nucleic acid sequences that encode the amino acid sequences depicted in the figures, or the complement thereof, as outlined herein. Hybridization conditions are further described below.

In a preferred embodiment, p42 polypeptide must share at least one epitope or determinant with the full length protein. By "epitope" or "determinant" herein is meant a portion of a protein which will generate and/or bind an antibody. Thus, in most instances, antibodies made to smaller p42 polypeptides will be able to bind to the full length protein. In another embodiment, antibodies made to native p42 polypeptide will bind to smaller p42 polypeptides, provided that the smaller polypeptides contain an epitope found on the full-length polypeptide that is recognized by the antibodies made to native p42 polypeptide. Accordingly, in a preferred embodiment p42 polypeptide is immunogenic.

By "immunogenic" or "immunogen" and grammatical equivalents herein is meant a substances that induces or evokes an immune response, such as a cell-mediated and/or humoral (antibody) immune response, in a mammal. In a preferred embodiment the immune response substantially reduces the symptoms and manifestations associated with plasmodium infection, as described herein.

As previously described herein, a p42 "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and/or deletions, as discussed below.

Included in the definition of p42 polypeptides are p42 polypeptide variants. These variants fall into one or more of three classes: substitutional, insertional or deletional variants. These variants ordinarily are prepared by site specific mutagenesis of nucleotides in the DNA encoding a p42 polypeptide, using cassette or PCR mutagenesis, scanning mutagenesis, gene shuffling or other techniques well known in the art, to produce DNA encoding the variant, and thereafter expressing the DNA in recombinant cell culture as outlined above. However, variant p42 polypeptide fragments having up to about 100–150 residues may be prepared by in vitro synthesis using established techniques. Amino acid sequence variants are characterized by the predetermined nature of the variation, a feature that sets them apart from naturally occurring allelic or interspecies variation of the p42 polypeptide amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed p42 polypeptide variants are screened for the optimal combination of desired activity. Techniques for making mutations at predetermined sites in DNA having a known sequence are well known. For example, the variations can be made using oligonucleotide-mediated site-directed mutagenesis [Carter et al., *Nucl. Acids Res.*, 13:4331 (1986); Zoller et al, *Nucl. Acids Res.*, 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)], all of which are expressly incorporated by reference, PCR mutagenesis, or other known techniques can be performed on the cloned DNA to produce the p42 polypeptide variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989), which is expressly incorporated by reference]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.* 150:1 (1976), which are expressly incorporated by reference]. If alanine substitution does not yield adequate amounts of variant, an isoteric amino acid can be used. Screening of the mutants or variants is done using assays of p42 polypeptide activities and/or properties as described herein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the p42 polypeptide are desired, substitutions are generally made in accordance with the following chart:

Chart I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the p42 polypeptide as needed, for example, to increase the immunogenicity of the p42 polypeptide. Alternatively, the variant may be designed such that the biological activity of the p42 polypeptide is not altered. For example, glycosylation sites may be added, altered or removed. p42 polypeptide may be designed to add phosphorylation sites.

p42 polypeptide fragments may be prepared by any of a number of conventional techniques. Desired peptide fragments may be chemically synthesized. An alternative approach involves generating p42 polypeptide fragments by enzymatic digestion, e.g., by treating the protein with an enzyme known to cleave proteins at sites defined by particular amino acid residues, or by digesting the DNA with suitable restriction enzymes, expressing the digested DNA and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, p42 polypeptide fragments share at least one biological and/or immunological activity with the native polypeptides shown in the figures.

In another aspect of the invention, as noted above, we have found that when a p42 amino acid sequence is expressed in tobacco plant cells, a pure product can be obtained without degradation or cleavage if DNA coding for a MAD allele sequence is employed. An amino acid sequence of the p42 antigen is considered to be of the MAD allele if it corresponds to the parts of gp195 of the MAD *Plasmodium falciparum* isolate which are dimorphic as compared with the amino acid sequences of the Wellcome and K1 isolates (Tanabe et al. (1987) *J. Mol. Biol.* 195:273). For example, gp195 of the FUP isolate is of the MAD allele (Chang et al. (1989) *Proc. Natl. Acad. Sci. USA* 86:6343; Chang et al. (1988) *Exp. Parasitol.* 67:1) (FUP isolate p42 amino acid sequence is as well).

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to the nucleic acid sequence of the figures is preferably greater than 75%, more preferably greater than about 80%, particularly greater than about 85% and most preferably greater than 90%. In some embodiments the sequence identity will be as high as about 93 to 95 or 98%.

In a preferred embodiment, a p42 nucleic acid encodes a p42 polypeptide. As will be appreciated by those in the art, due to the degeneracy of the genetic code, an extremely large number of nucleic acids may be made, all of which encode the p42 polypeptides of the present invention. Thus, having identified a particular amino acid sequence, those skilled in the art could make a number of different nucleic acids by modifying the sequence of one or more codons in a way which does not change the amino acid sequence of the p42 polypeptide. As indicated herein, however, the identification and selection of a nucleic acid sequence appropriate for optimal expression in a given system can require significant trial and error and inventive input.

In one embodiment, a p42 polypeptide is identified as being encoded by a nucleic acid that hybridizes under high stringency to the nucleic acid sequences shown in the figures, or their complement. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences specifically hybridize at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993), which is expressly incorporated by reference. Generally, stringent conditions are selected to be about 5–10° C. lower than the thermal melting point ($T_m$) for the specific sequence at a defined ionic strength, pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at about pH 7.0 to 8.3 and the temperature is at least about 30° C. for short probes (e.g., about 10 to 50 nucleotides) and at least about 60° C. for long probes (e.g., greater than about 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

As used herein and further defined below, "nucleic acid" may refer to either DNA or RNA, or molecules which contain both deoxy- and ribonucleotides. The nucleic acids include genomic DNA, cDNA, and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the figures also include the complement of the sequence.

By the term "recombinant nucleic acid" herein is meant nucleic acid, originally formed in vitro or in a cell in culture, in general, by the manipulation of nucleic acid by endonucleases and/or exonucleases and/or polymerases and/or ligases and/or recombinases, to produce a nucleic acid not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Any p42 coding DNA can be used to make the plant expression vector. Thus, non-natural DNA sequences, different from the particular ones listed herein, can be used effectively in practicing the invention. For example, given the degeneracy of the genetic code DNA sequences encoding a protein can be modified to optimize expression for particular organisms and/or cells types, such as, tailoring the codon usage to those codons that are preferred by a given expression system, without modifying the desired amino acid sequence of the expressed protein.

Similarly, non-natural amino acid sequences can be coded for by the DNA used in the plant expression vector in order to obtain functional products that obtain the advantages of the invention. It is further within the scope of the invention to delete portions of the p42 amino acid sequence which do not affect the beneficial result obtained with the NtMSP1.42 products exemplified herein.

The polypeptide may be produced as either a fusion product, such as a heterologous protein containing part NtMSP1.42 amino acid sequence fused to *Plasmodium falciparum* sequence, or the product may merely contain a *Plasmodium falciparum* sequence. Methods of making both types of proteins are well known to one skilled in the art.

Accordingly, in a preferred embodiment, the invention provides fusion polypeptides comprising a, first, p42 polypeptide and at least a second polypeptide, wherein the second polypeptide is a p42 polypeptide, as defined herein, or a heterologous polypeptide. The p42 polypeptide and second polypeptide are fused covalently or non-covalently, with covalently being preferred. As will be appreciated by those in the art, the fusion polypeptides of the invention can be configured in a variety of ways. In one embodiment, the p42 polypeptide is fused to the carboxy terminus of the second polypeptide. Alternatively, the p42 polypeptide is fused to the amino-terminus of the second polypeptide. In another alternative embodiment, the p42 polypeptide is at a position internal to the carboxy and amino termini or the second polypeptide. Accordingly, the p42 polypeptide and the second polypeptide are joined to produce linear fusions or branched fusions in any manner as the biology and activity permits, although in general, N- or C-terminal fusions are preferred to internal fusions.

In general, the fusion polypeptides of the invention can be made either recombinantly or synthetically.

In a preferred embodiment, the p42 and second polypeptides are attached through the use of functional groups on each that can then be used for attachment. Preferred functional groups for attachment are amino groups, carboxy groups, oxo groups and thiol groups. These functional groups can then be attached, either directly or indirectly through the use of a linker. Linkers are well known in the art; for example, homo-or hetero-bifunctional linkers as are well known (see 1994 Pierce Chemical Company catalog, technical section on cross-linkers, pages 155–200, incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and C2 alkene being especially preferred. Suitable crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]propioimidate. Accordingly, at least one amino acid that reacts with a crosslinking agent may be added to a p42 polypeptide or the second polypeptide antibody by insertion and/or substitution to facilitate crosslinking.

In a preferred embodiment, the p42 and second polypeptides are crosslinked to a third molecule, which accordingly provides a scaffold for linking the p42 and second polypeptides. Suitable scaffolds include, for example, peptides, carbohydrates, nucleic acids, lipids, small organic molecules and the like. The crosslinkers function to join the p42 and second polypeptide and preferably allow each component to function without interference from the other component or the crosslinker.

In one embodiment, linear fusions are preferred. Accordingly, the p42 polypeptide is directly fused either to the amino terminus, carboxy terminus, and/or is internal to the termini of the second polypeptide. In a preferred embodiment, linkers, spacers, or adapters comprised of amino acids are used to join the p42 polypeptide and second polypeptide. In some embodiments, the fusion nucleic acid optionally encodes linkers, crosslinkers, spacers, or adapters, as needed. The number of amino acids comprising the linker can be determined by routine experimentation by a skilled artisan. The linkers comprising a sufficient number of amino acids such that the p42 and second polypeptides function without interference from the other. Accordingly, amino acids that comprise the linker preferably do not substantially alter biological activity of the p42 or second polypeptide.

For example, useful linkers include glycine polymers $(G)_n$, glycine-serine polymers (including, for example, $(GS)_n$, $(GSGGS)_n$ (SEQ ID NO:17) and $(GGGS)_n$ (SEQ ID NO:18), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted than residues with longer side chains (see Scheraga, Rev. Computational Chem. III73–142 (1992), expressly incorporated by reference). Secondly, serine is hydrophilic and therefore able to solubilize what could be a globular glycine chain. Third, similar chains have been shown to be effective in joining subunits of recombinant proteins such as single chain antibodies.

In a preferred embodiment, either or both p42 and the second polypeptide of the invention can comprise additional components or may be modified in other ways. For example, modification of the fusion polypeptides include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "amino groups of lysine, arginine, and histidine side chains [T. E. Creighton, *Proteins: Structure and Molecular Properties*, W. H. Freeman & Co., San Francisco, pp. 79–86 (1983), expressly incorporated by reference], acetylation of the N-terminal amine, and amidation of any C-terminal carboxyl group.

Another type of covalent modification of the p42 and second polypeptide included within the scope of this invention comprises altering the native glycosylation pattern of the polypeptide. "Altering the native glycosylation pattern" is intended for purposes herein to mean deleting one or more carbohydrate moieties found in native sequence of the fusion polypeptide components, and/or adding one or more glycosylation sites that are not present in the native sequences.

Addition of glycosylation sites may be accomplished by altering the amino acid sequence thereof. The alteration may be made, for example, by the addition of, or substitution by, one or more serine or threonine residues to the fusion polypeptide sequence (for O-linked glycosylation sites). The alteration also may be made, for example, by the addition of, or substitution by one or more Asn-Xaa-Ser/Thr sites (Xaa=any amino acid; for N-linked glycosylation sites) in the fusion polypeptide sequence. The fusion polypeptide amino acid sequence may optionally be altered through changes at the DNA level, particularly by mutating the DNA encoding the p42 polypeptide at preselected bases such that codons are generated that will translate into the desired amino acids.

Another means of increasing the number of carbohydrate moieties on the fusion polypeptide is by chemical or enzymatic coupling of glycosides to the polypeptide. Such methods are described in the art, e.g., in WO 87/05330 published 11 September 1987, and in Aplin and Wriston, *CRC Crit. Rev. Biochem.*, pp. 259–306 (1981), all of which are expressly incorporated by reference.

Removal of carbohydrate moieties present on p42 or the fusion polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981), all of which are expressly incorporated by reference. Enzymatic cleavage of carbohydrate moieties on polypeptides can be achieved by the use of a variety of endo-and exo-glycosidases as described by Thotakura et al., *Meth. Enzymol.*, 138:350 (1987), expressly incorporated by reference.

Another type of covalent modification of p42 or the fusion polypeptide comprises linking the p42 or fusion polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337, all of which are expressly incorporated by reference.

In one embodiment, the p42 polypeptide is fused to an epitope tag which provides an epitope to which an anti-tag antibody can selectively bind. The epitope tag is generally placed at the amino-or carboxyl-terminus of the p42 polypeptide but may be incorporated as an internal insertion or substitution as the biological activity permit. The presence of such epitope-tagged forms of a p42 polypeptide can be detected using an antibody against the tag polypeptide. Also, provision of the epitope tag enables the p42 polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988), which is expressly incorporated by reference]; the c-myc tag and the 8F9, 3C7, 6E10, G4, B7 and 9E10 antibodies thereto [Evan et al., *Molecular and Cellular Biology*, 5:3610–3616 (1985), which is expressly incorporated by reference]; and the Herpes Simplex virus glycoprotein D (gD) tag and its antibody [Paborsky et al., *Protein Engineering*, 3(6):547–553 (1990), which is expressly incorporated by reference]. Other tag polypeptides include the Flag-peptide [Hopp et al., *BioTechnology*, 6:1204–1210 (1988), which is expressly incorporated by reference]; the KT3 epitope peptide [Martin et al., *Science*, 255:192–194 (1992), which is expressly incorporated by reference]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA* 87:6393–6397 (1990), which is expressly incorporated by reference] and the histidine tag and metal binding sites (Smith, Ann. NY. Acad. Sci., 646:315–321 (1991), which is expressly incorporated by reference], with the Flag and histidine tag being preferred.

In a preferred embodiment, nucleic acid encoding a leader sequence can be included in the expression vector and fused to the amino terminus of the p42 polypeptide to facilitate sorting through the endoplasmic reticulum and proper folding of the polypeptide product. For example, cDNA encoding an upstream leader sequence can be inserted 5' to the p42 coding region using conventional techniques. The final purified product according to the invention may include a leader sequence, or the sequence may be cleaved during expression. Amino-terminal amino acid sequencing indicates that the polypeptide is appropriately cleaved.

The many variations in techniques for expressing and isolating p42 will be apparent to one skilled in the art. For example, promoters known in the art can be modified to alter expression. In addition, the number and composition of the nucleotides in the region between the promoter and start of the open reading frame can be modified to alter expression.

The p42 polypeptide product can be conventionally purified, such as, in part, by affinity chromatography with a Mab specific for natural p42. Mab 5.2 is one such antibody. In another embodiment, p42 polypeptide can be purified, for example, by the addition of a tag to the p42 polypeptide as described herein, preferably at the carboxy terminus, and purified by the appropriate affinity purification methods.

The p42 polypeptide obtained is a variant of naturally occurring p42 that results from characteristic post-translational processing occurring in plant cells, especially *Nicotiana tabacum cv. xanthi* cells.

The present invention is further described in the examples below. The examples are for illustration purposes, and are not intended to limit the scope of the invention. All patents, patent applications, and publications and references cited therein are hereby expressly incorporated by reference in their entirety.

EXAMPLES

Example 1

MSP1.42 FUP Construct

Materials and Methods

Construction of Plant Expression Vectors

Figure 1B:
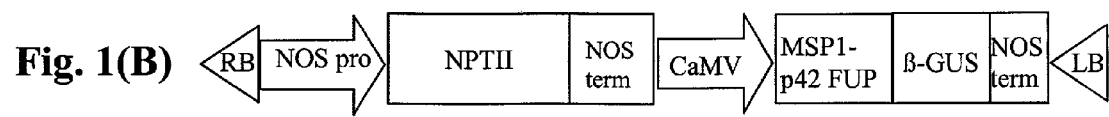
Figure 1C:
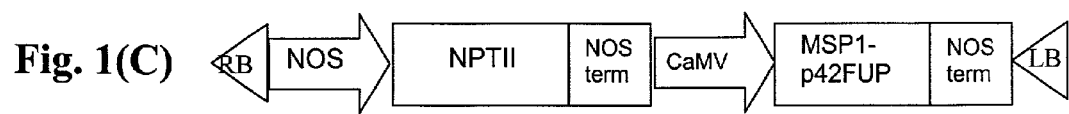

The recombinant MSP1.42 FUP construct and antigens are based on the C-terminal 42 kD sequence of the *P. falciparum* Uganda-Palo Alto isolate (FUP) corresponding to the MAD20 allele. MSP1.42 expression constructs were generated by ligation of the FUP MSP1.42 gene into the expression vector pBI121 (Clontech) (FIGS. 1A–D) or modifications of this vector. The pUC18 plasmids which contained the FUP gene was constructed previously from *P. falciparum* genomic DNA. (Chang et al. 1992. Journal of Immunology 149:548; Nishimura et al. 1999. Tropical Medicine and Medical Microbiology, University of Hawaii at Manoa: Honolulu). MSP1.42 FUP was excised by BamH1 and Sac1 from pUC18 and ligated into BamH1-Sac1 sites within the multiple cloning site of pBI121(FIG. 1A), which contains the GUS gene (MSP1.42a, FIG. 1B), or of pBI121, which lacks GUS (pBI121 without b-GUS) (MSP1.42b, FIG. 1C). The MSP1.42 FUP plant expression construct sequence described above was confirmed by DNA sequencing (data not shown).

Tobacco Transformation

Binary vector constructs for pBG-MSP1.42a and pBI-MSP1.42b were prepared from TOP10F' cultures and were individually transferred by electroporation into *Agrobacterium tumefaciens* strain LBA4404. Plasmids from LBA4404 transformants were isolated and inserts were verified by PCR. *Nicotiana tabacum cv. xanthi* were transformed by the co-cultivation procedure and transgenic plants were selected on medium containing 300 mg/L kanamycin. Plant transformation was confirmed as described below.

Nucleic Acid Analysis

Plant tissue genomic DNA extraction was performed as described by Doyle and Doyle (Doyle et al. 1990. Focus12: 13). DNA was quantified using a fluorometer (Dynaquant 200, Hoefer Scientific Instruments, San Francisco, Calif.) and 20 µg DNA was digested with 50 U of the appropriate restriction enzyme. Southern blots were performed according to Sambrook (Sambrook, J., E. F. Fritsch, T. Maniatis, Molecular cloning: a laboratory manual. 1989, Cold Spring Harbor, N.Y.: Cold Spring Harbor Laboratory).

Total RNA was purified according to the Tri-Reagent protocol (Sigma, St. Louis, Mo.). Northern blot analysis using 15–20 µg total RNA per sample were performed according to Church and Gilbert (Church et al. 1991. Proc Natl Acad Sci USA 81:1991) with modifications according to the downward blot procedure using the Nytran® Super-Charge TurboBlotter™ (Schleicher-Schuell, Keene, N.H.).

Probes for Northern and Southern hybridizations were made using 25 ng of MSP1.42 FUP and 50 mCi dATP as per the Prime-a-Gene® kit (Promega, Madison, Wis.). Unlabeled probe was removed using an Elutip-D® column (Schleicher and Schuell). The amount of radiolabeled probe was assessed by scintillation counting and a volume equivalent to 10×106 cpm was added to the pre-hybridization buffer for hybridization to Northern or Southern blots and incubated for 12 hours at 65° C. or as described in the text.

Analysis of MSP1.42 Protein Level In Transgenic Plants

Protein analysis was performed using two methods. In the first method, juvenile leaf discs (24.8±6 mg leaf tissue) were crushed in a 1.5 ml microfuge tube on ice with a pestle in the presence of 150 μl of P-BBS buffer [(BBS: 0.16 M boric acid, 0.13 M sodium chloride, 0.027 M sodium hydroxide, pH 8.0) containing 0.1% Triton x-100 and 1 mM phenyl-methanosulfonyl-fluoride (PMSF).

In the second method, mature leaves (10±5 g leaf tissue) were crushed to a powder with mortar and pestle in liquid nitrogen and 20 ug of the powder was added to 100 ml of P-BBS containing 2 g Polyvinylpyrollidone (40) (Sigma, Mo.) and 5 mM EDTA (pH 8.0). The slurry was incubated for 1 hr with agitation at 4° C. This slurry was poured through fine nylon screen, centrifuged at 10,000×G and the supernatant was recovered. Immunochromatography was performed using mAb 5.2 bound to Sepharose Protein G (Siddiqui et al. 1987. Proc Natl Acad Sci USA, 84:3014). The plant extracts were incubated with MAb-coated Sepharose Protein G for 12 h at 4° C. with agitation. The Sepharose-protein mixture was poured into a column and washed with 10 volumes BBS. NtMSP1.42S protein was eluted using 0.1 M glycine (pH 2.6), and immediately neutralized with 1.0 M Tris-HCl, pH 8.0. Chromatography fractions and crude leaf disc supernatants were electrophoresed in non-denaturing SDS-PAGE, and evaluated by immunoblot analysis using mAb 5.2. Following the primary antibody, rabbit anti-mouse (1/10000; Zymed, South San Francisco, Calif.) was used as a secondary antibody and an alkaline phosphotase (AP) labeled goat anti-rabbit antibody (1/10000; Zymed) was administered as a tertiary antibody. BCIP/NBT (5-Bromo-4-chloro-3-Indolyl Phosphate/Nitroblue Tetrazolium; Kierkegaard & Perry Laboratories, Gaithersburg, Md.) was employed as a substrate for the AP.

Results

MSP1.42 FUP in pBI121

Two plasmid constructs containing the full length, original MSP 1.42 FUP sequence in the pBI121 vector, are illustrated in (FIGS. 1B and 1C). In the first construct, MSP1.42a, the bacterial β-Glucuronidase gene (GUS) was retained downstream of MSP1.42 FUP. In the second construct, MSP1.42b, GUS was removed from the expression cassette. Restriction digests of the two constructs with BamHI excised 1.2 kB bands, verifying that a fragment of the correct size was inserted into the plant transfer plasmid. In addition, DNA sequence analysis confirmed the identity and sequence of the inserts of these constructs.

Two plants expressing both MSP1.42 FUP constructs and one wild type tobacco plant were analyzed by Southern blot using plant genomic DNA digested by either BamH1 or Sac1. BamH1 should have excised the entire 1.2 kb MSP1.42 FUP gene, serving as an indicator of complete and intact MSP1.42 FUP integration into the plant genome. Sac1 should have cut downstream of the GUS gene and at unknown sites within the genome to generate one band or multiple bands, thus serving as an indicator of single or multiple integration events. Southern blots of these transgenic plants resulted in the detection of a number of different sized fragments (FIG. 3A). For BamH1 digested samples, wild type DNA (lane 1) showed a very faint background band at around 9 kB; MSP1.42FUPa plant 1 DNA (lane 2) revealed a band of approximately 8 kB; MSP1.42FUa plant 2 DNA (lane 3) contained several bands of 5, 7 and 8 kB, respectively; MSP1.42FUb plant 1 (lane 4) had a band at 9 kB, and MSP1.42FUb plant 2 (lane 5) appeared to have no hybridizing bands. None of the plants appeared to contain the expected 1.2 kB BamHI hybridizing band. For the samples digested with Sac1, the wild type plant (lane 6) had no visible bands; lane 7 revealed a faint 9 kB band; lane 8 illustrated a band at approximately 7 kB; lane 9 showed a 7kB band and an 8 kB band; lane 10 possessed three bands, a 9 kB band and two faint bands at 7 kB and 8 kB respectively (FIG. 3A).

The presence of strongly hybridizing bands in Southern blots of most of the transgenic plants suggested that they contained one or more integrated copies of the MSP1.42 FUP related inserts. However, the failure to detect the expected 1.2 kB BamH1 fragment in any of these plants suggested that the inserts either were incomplete fragments of the MSP1.42 gene or that one or both of the BamHI sites were destroyed during the process of integration. Because of these inconclusive BamHI digest results, it was difficult to interpret the results of the corresponding SacI digests. Northern blot analysis of plants containing both MSP1.42 FUP constructs revealed several RNA species (FIG. 3B). The expected size of mature mRNA was 1.2 kB for the MSP1.42FUPb construct and 3.0 kB for the MSP1.42FUPa construct, but the size of the predominant band observed in most plants was estimated to be 700 bp (FIG. 3B, lanes 1 to 5). In one sample containing MSP1.42+GUS (lane 5), bands of approximately 9 kB and 700 bp were observed. The wild type plant analyzed in these studies (lane 6) was negative.

Upon closer examination of the FUP MSP1.42 DNA sequence, it was noted that the sequence contained several cryptic intron splice sites which may have interfered with the production of full-length MSP1.42 transcripts.

Protein Analysis from MSP1.42 FUP Constructs

Western blots using monoclonal or polyclonal antibodies specific for parasite MSP-1 p42 resulted in no visible bands in the MSP1.42 FUP transgenic plants and in wild type plants (data not shown).

Discussion

A series of genetic modifications were required to ultimately achieve expression of the MSP1.42 polypeptide in transgenic plants. In the first attempt to express MSP1.42 in plants, a construct containing the natural MSP1.42 FUP sequence to transform tobacco was used. Transgenic plants were generated that were antibiotic resistant, indicating that the expression cassette was integrated into the plant genome. Probe-specific inserts of various sizes were found in these transgenic plants, however none were of the expected 1.2 kB size. Analysis of these plants by Northern blot generally revealed very low levels of probe-specific transcripts, usually half of the expected size, although one plant produced a 9.0 kB hybridizing transcript. Immunoreactive MSP1.42 protein was not detected in any of these plant extracts. Upon examination, cryptic intron splice sites were identified in the FUP MSP1.42 coding region that had been determined to interfere with gfp expression in plants (Haseloff et al. 1997. Proc Natl Acad Sci USA 94(6): 2122).

In addition to the presence of specific sequences reported to affect RNA transcription and stability, the FUP MSP1.42 sequence is characterized by an extremely high A:T content (70%) which is characteristic of *Plasmodium* genes. This property contrasts with tobacco and other plant genes, which contain approximately 50% A:T. This high A:T ratio resulted in the presence of a number of plant-recognized RNA instability sequences, AUUUA, within the MSP1.42 FUP gene. These sequences, normally found in 3' untranslated regions of plant genes, are located within the p42 coding region, and have been shown by others to produce instability of foreign gene mRNA within plants (Ohme-Takagi et al.

1993. Proc Natl Acad Sci USA 90(24): 11811; Iannacone et al. 1997 Plant Mol Biol 34(3):485). Upon further investigation, one potential poly-adenylation signal also was discovered within the FUP allele sequence which had not been previously recognized. Premature poly-adenylation has been shown to impact the expression of some foreign proteins in plants (Haffani et al. 2000. Mol Gen Genet 264(1–2):82), and it was suspected that this sequence was affecting expression in these plants as well.

Example 2

MSP1.42 FVO Construct

Materials and Methods

Construction of Plant Expression Vectors

Figure 1D:
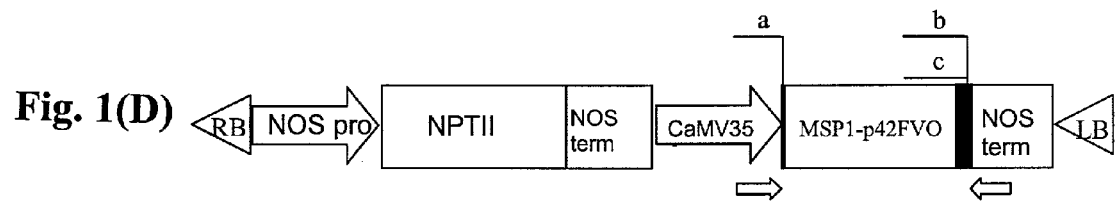

The MSP1.42 FVO construct and antigens are derived from the C-terminal 42 kD sequence of a Thailand isolate (FVO) corresponding to the K1 allele (Tanabe et al. 1987. J Mol Biol 195:273). MSP1.42 expression constructs were generated by ligation of the FVO MSP1.42 gene into the expression vector pBI121 (Clontech) (FIG. 1) or modifications of this vector. The pUC18 plasmids which contained the FVO MSP1.42 gene were constructed previously from *P. falciparum* genomic DNA. (Chang et al. 1992. Journal of Immunology 149:548; Nishimura et al. 1999. Tropical Medicine and Medical Microbiology, University of Hawaii at Manoa: Honolulu). MSP1.42 FVO was excised from pUC18 using BamH1 and Kpn1 and amplified by PCR using Pfx polymerase (Life Technologies). Oligonucleotides were used to modify the 5' end of the MSP1.42 FVO sequence and to create two different 3' regions (FIG. 1D). The 5' oligonucleotide (5' CGGGATCCC AAGGAGATACC ATGGCAGTA ACTCCTTCC 3'; SEQ ID NO:5) served to remove the flg5 secretion signal present in the original MSP1.42 constructs. The first 3' oligonucleotide (5' CTGCGAGC TCTTATTAAA GCTCATC ATGCTGCAGAAA ATACC 3'; SEQ ID NO:6) included an HDEL region (MSP1.42FVO-ER, underlined). The second 3' oligonucleotide (5' CTGCGAGCT CTTATTA ATG ATGATGATG 3'; SEQ ID NO:7) contained a histidine rich region (MSP1.42FVO-His, underlined). These two amplified MSP1.42 FVO fragments were then inserted using the Bam-H1 and Sac1 sites of pBI121 without b-GUS (FIG. 1D). The MSP1.42FVO plant expression construct sequence described above was confirmed by DNA sequencing (data not shown).

Tobacco Transformation

Binary vector constructs pBG-MSP1.42b and pBI-MSP1.42a were prepared from TOP10F' cultures and were individually transferred by electroporation into *Agrobacterium tumefaciens* strain LBA4404. Plasmids from LBA4404 transformants were isolated and inserts were verified by PCR. *Nicotiana tabacum cv. xanthi* were transformed by the co-cultivation procedure and transgenic plants were selected on medium containing 300 mg/L kanamycin. Plant transformation was confirmed as described below.

Nucleic Acid Analysis

Nucleic acid analysis was performed using the methods described in Example 1. Probes for Northern and Southern hybridizations were made using 25 ng of MSP1.42FVO and 50 mCi dATP as per the Prime-a-Gene® kit (Promega, Madison, Wis.).

Analysis of MSP1.42 Protein Level In Transgenic Plants

Protein analysis of MSP1.42 was performed using the methods described in Example 1.

Results

FVO in pBI

The MSP1.42 FVO allelic sequence was utilized because cryptic intron splice sites were not present in this sequence. MSP1.42 FVO was amplified from pUC18 by PCR using pfx polymerase and appropriate primers to create a 5' BamH1 restriction site, transcription initiation codon sequence, ribosomal binding sequence and optimal codons surrounding the AUG translation start site for plant expression (Helliwell et al., 1995. Plant Mol Biol, 1995. 29:621). Primers were also designed to create two alternative 3' regions containing either a) six histidines followed by two stop codons and a Sac1 restriction site (MSP1.42FVO-His), or b) H-D-E-L codons (associated with targeting to the endoplasmic reticulum) followed by two stop codons and a Sac1 restriction site (MSP1.42FVO-ER). Additionally, the GUS sequence was removed from pBI121 by digestion with BamH1 and Sac1 (pBI121 without b-GUS). The MSP1.42 FVO sequences were then ligated into the BamH1-SacI sites of the vector as illustrated in FIG. 1D to produce the MSP1.42FVO-ER and MSP1.42FVO-His constructs.

Figure 4A:
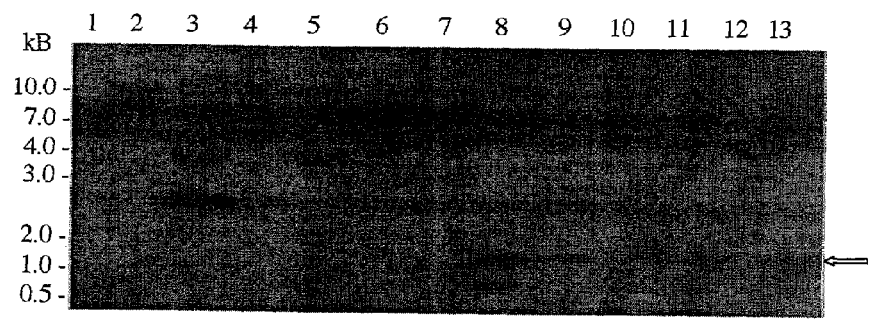
FIGS. 4A–B show analysis of MSP1.42 gene DNA integration and transcription in plants transformed with MSP1.42FVO-ER and MSP12.42FVO-His expression constructs. 32[P]-labeled MSP1.42FVO was used as the hybridization probe. (A) Southern blot of wild type plant DNA digested with BamHI (lane 1), MSP1.42FVO-His transformants digested with BamHI (lanes 2–4) or with BamHI+ Sac1 (lanes 8–10), and MSP1.42FVO-ER transformants digested with BamHI (lanes 5–7) or BamHI+Sac1 (lanes 8–13). (B) Northern blot of wild type plant RNA (lane 1), MSP1.42FVO-His transformants (lanes 2–4) and MSP1.42FVO-ER transformants (lanes 5–7). Arrows indicate the expected fragment sizes.
Figure 4B:
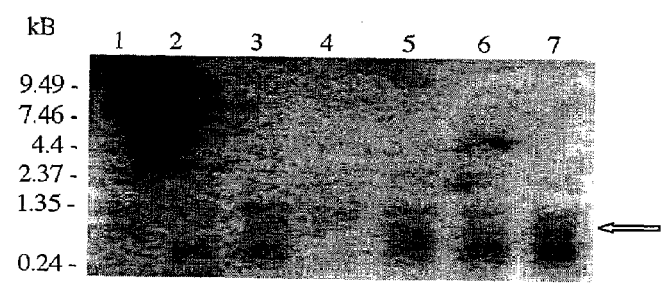

Integration of MSP1.42FVO-ER or MSP1.42FVO-His into the plant genome was assessed by Southern blot using a 32[P]-labeled MSP1.42 FVO DNA probe (FIG. 4A). Genomic DNA was isolated from three plants transformed with each MSP1.42 FVO construct and digested by BamH1 or both BamH1 and Sac1 restriction enzymes. Wild type plant DNA was also isolated and digested with BamH1 alone. BamH1 and Sac1 digests should have generated a 1.2 kB band upon excision of the modified MSP1.42 FVO gene, indicating successful MSP1.42 FVO insertion into the genome. Bam-H1 should have cut upstream of the modified MSP1.42 FVO gene and within the genome to generate a band or multiple bands of unknown size. Thus, in these transformants, BamHI digestion should illustrate single or multiple integration events. Southern blots resulted in a number of different fragment sizes (FIG. 4A). In the case of MSP1.42FVO-His transformants, genomic DNA samples digested by BamH1 and Sac1 contained both the expected 1.2 kB bands and additional bands: lane 8 had a band at 1.2 and light band at 0.8 kB; lane 9 showed two bands, one at 1.2 and another at 0.5 kB; and lane 10 showed one band at approximately 4.5 kB. For MSP1.42FVO-ER transformants, similar results were obtained: lanes 11 and 13 contained a single band at 1.2 kB and lane 12 revealed a dark band at 1.2 and two bands of lesser intensity at 4 and 7 kB respectively (FIG. 4A).

For the BamH1 digested samples: wild type DNA in lane 1 showed no bands; lane 2 (MSP1.42FVO-His) has a doublet of 9 and 10 kB respectively; lane 3 (MSP1.42FVO-His) revealed bands at 2.5, 4, 10 kB and a faint band at 12 kB; lane 4 (MSP1.42FVO-His) had only one light band at approximately 12 kB. Lane 5 (MSP1.42FVO-ER) showed a single band at 4.0 kB; lane 6 (MSP1.42FVO-ER) had a dark band at 7 kB and a lighter one at 4.5 kB and lane 7 (MSP1.42FVO-ER) had a doublet at 7 and 10 kB. Wild type plant genomic DNA cut with BamH1 showed no hybridizing bands, indicating that there are no tobacco genes which cross-hybridize with the probe and that background binding was low. In summary, 5 of 6 samples digested by BamH1 and Sac1 contained the expected 1.2 kB hybridizing band. At least one plant (lanes 5 and 11) appeared to have a single insert of the appropriate size (arrow in FIG. 4A). These results indicated that the full-length MSP1.42 FVO constructs were more readily integrated into the plant genome than the previous MSP1.42 FUP constructs (FIG. 4A). Southern blots of DNA digested by BamH1 illustrated several examples of multiple integration events (lanes 2, 3, 6 and 7). PCR of transgenic plant genomic DNA with insert-specific primers resulted in the amplification of a 1.2 kB band that was not detected in similar experiments with wild type genomic DNA (data not shown).

RT-PCR reactions of MSP1.42FVO-His and MSP1.p4KER mRNA were negative using primers specific for the 5' and 3' ends of the insert. In contrast, control fragments of the appropriate size were amplified in control RT-PCR reactions of the same samples using primers for the plant violaxanthin deepoxidase gene, indicating plant RNA integrity. The presence of ribosomal RNA bands on an agarose gel also indicated the absence of generalized RNA degradation (data not shown).

A Northern blot of adult transgenic plants containing either of the modified MSP1.42 FVO constructs revealed MSP1.42-related RNA transcripts (FIG. 4B). In these studies, mRNA was isolated from the same three plants described above which had been produced with each modified MSP1.42 FVO construct and one wild type plant. The expected size of mature MSP1.42 mRNA for these transformants was 1.2 kB. Exposure of Northern blots for up to 7 days revealed no distinct, 1.2 kB bands (FIG. 4B, arrow). Northern blots of wild type mRNA (lane 1) contained a faint smear ranging from 0.8 to 1.35 kB. The results for mRNA from three plants transformed with the MSP 1.42FVO-His construct (lanes 2–4) were similar to the wild type, but in lanes 2 and 3 an additional, distinct band could be visualized at approximately 0.5 kB. Samples from MSP1.42FVO-ER transformants (FIG. 4B, lanes 5–7) all contained an intense hybridizing band at approximately 0.5 kB and additional bands at 1 and 1.35 kB respectively. One MSP1.42FVO-ER transformant (FIG. 4B, lane 6) appeared to have a band at 4 kB.

Protein Analysis from MSP1.42 FVO Constructs

Western blots using monoclonal or polyclonal antibodies specific for parasite MSP-1 p42 resulted in no visible bands in MSP1.42 FVO transgenic plants and in wild type plants (data not shown).

Discussion

New constructs utilizing the MSP1.42 FVO sequence, which lack the FUP MSP1.42 coding region cryptic intron splice sites (e.g., Example 1), were evaluated. The MSP1.42 FVO sequence also was modified to enhance translation by the addition of plant-specific translation initiation codons, a ribosomal binding site and optimization of the AUG translation start site within the 5' upstream region. Constructs were prepared which contained either an endoplasmic reticulum retention signal (HDEL (SEQ ID NO:19)) or a hexa-Histidine region within the 3' terminus of MSP1.42 FVO. The majority of transgenic plants recovered in experiments containing the MSP1.42 FVO sequence had an insert of the expected 1.2 kB size although one anomalous plant contained a larger insert. Despite these modifications, these transgenic plants also produced low levels of MSP1.p42-related mRNA products of approximately half the expected size. Furthermore, these plants did not contain any material reacting with antibodies against native MSP1.42. Therefore, although integration of the complete MSP1.42 gene appeared to occur with these new constructs, the sequence alterations intended to enhance translation and the omission of cryptic intron splice sites within the FVO allele were still insufficient for gene expression.

In addition to the presence of specific sequences reported to affect RNA transcription and stability, the FVO MSP1.42 sequence is also characterized by an extremely high A:T content (74%) which is characteristic of *Plasmodium* genes. As with the FUP MSP1.42 sequence (e.g., Example 1), this high A:T ratio resulted in the presence of a number of plant-recognized RNA instability sequences, AUUUA, within the MSP1.42 FVO gene. Upon further investigation, one potential poly-adenylation signal also was discovered within the FVO MSP1.42 allele sequence which had not been previously recognized. As previously indicated, premature poly-adenylation has been shown to impact the expression of some foreign proteins in plants, and it was suspected that this sequence was affecting expression in the FVO MSP1.42 plants as well.

Example 3

NtMSP1.42 Construct

Materials and Methods

Construction of Plant Expression Vectors

The modified MSP1.42 FUP (NtMSP1.42) gene had been re-engineered previously to reflect insect cell codon usage for baculovirus expression studies and inserted into pUC18. See co-pending U.S. patent application Ser. No. 09/500,376, herein incorporated by reference. This modified MSP 1.42 sequence was used as a template for high fidelity PCR to create the NtMSP1.42-pBG constructs (FIG. 2). NtMSP1.42 expression constructs were created by insertion into either pBI121 without b-GUS or pBINmGFP5-ER without mGFP5-ER (Haseloff et al. 1997. Proc Natl Acad Sci USA 94:2122) (e.g., modified to delete the gfp gene). Two versions, a secretion construct (NtMSP1.42S) and a cytoplasmic construct (NtMSP1.42C), were created which differed in their 5' regions but maintained the same 3' region (FIG. 2). The 5' region of the NtMSP1.42 sequence (A) was altered by removing the flg5 yeast secretion signal while maintaining the BamH1 site and including a translation initiation codon sequence (TICS), a ribosomal binding site (RBS) and altering the bases surrounding the translation initiation sequence to correspond to sequences optimal for plant expression (Haseloff et al. 1997. Proc Natl Acad Sci USA94:2122). In the NtMSP1.42S construct, a 23 amino acid *Arabidopsis thaliana* basic chitinase signal sequence (Haseloff et al. 1997. Proc Natl Acad Sci USA94:2122) was present within pBINmGFP5-ER without mGFP5-ER and kept upstream of NtMSP1.42 gene. The 3' region (B) was modified by removing an engineered hexa Histidine region and replacing it with the endoplasmic reticulum retention signal (HDEL), two stop codons and a Sad1 site.

For the cytoplasmic construct, the 5' oligonucleotide used was: 5' GGTGAGCTC TTAAAGCTC ATCATGGGA GCAGAAGAT ACCGTC 3' (SEQ ID NO:8). For the secretory construct, the 5' oligonucleotide was: 5' GCCGAATTC GACAACATCC TCAGT 3' (SEQ ID NO:9). In both cases, the 3' oligonucleotide was: 5' GGTGAGCTCTT AAAG CTCATCATGGGA GCAGAAGAT ACCGTC 3' (SEQ ID NO:10). A single "AUUUA" instability sequence was found in the NtMSP1.42 sequence and was removed by PCR using the 5' primer described above and a 3' primer which conservatively removed this instability sequence (5' AGAGCTAAT GTGCTTGAAT TGCATAAGGTC 3'; SEQ ID NO:11). A second PCR was performed using the NtMSP1.42 gene as a template, a forward primer that removed the instability sequence (5' GACCTTATG CAAT-TCAAG CACATTAGC TCT 3'; SEQ ID NO:12) and the 3' primer described above. The products of these two PCR reactions were then used as templates to generate both secretory and cytoplasmic full-length gene constructs using appropriate 5' and 3' primers. The full-length cytoplasmic product was ligated into the BamH1 and Sac1 sites of pBI121 without b-GUS. The full-length secretory product was ligated into EcoR1 and Sac1 sites of pBINmGFP5-ER without mGFP5-ER. The NtMSP1.42 plant expression construct sequence described above was confirmed by DNA sequencing (data not shown).

Tobacco Transformation

Binary vector constructs pBIN-NtMSP1.42S and pBG-NtMSP1.42C were prepared from TOP10F' cultures and were individually transferred by electroporation into *Agrobacterium tumefaciens* strain LBA4404. Plasmids from LBA4404 transformants were isolated and inserts were verified by PCR. *Nicotiana tabacum cv. xanthi* were transformed by the co-cultivation procedure and transgenic plants were selected on medium containing 300 mg/L kanamycin. Plant transformation was confirmed as described below.

Nucleic Acid Analysis

Nucleic acid analysis was performed using the methods described in Example 1. Probes for Northern and Southern hybridizations were made using 25 ng of NTMSP1.42 and 50 mCi dATP as per the Prime-a-Gene® kit (Promega, Madison, Wis.).

Analysis of MSP1.42 Protein Level In Transgenic Plants

Protein analysis of MSP1.42 was performed using the methods described in Example 1.

Results

NtMSP1.42 in pBI

Figure 2:
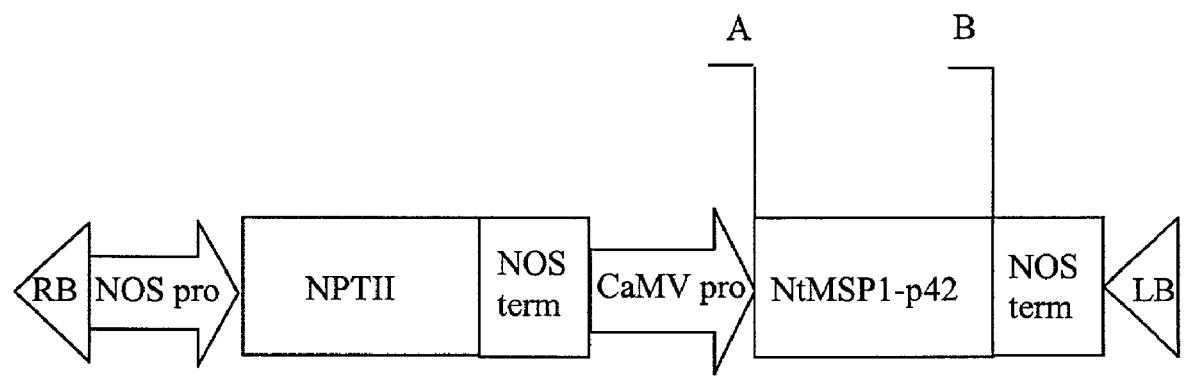
FIG. 2 depicts NtMSP1.42 expression constructs utilizing a re-engineered MSP1.42 FUP gene whose nucleotide sequence had been modified previously to conform to an insect cell codon usage which lowered the A:T content and removed cryptic introns.
Figure 3A:
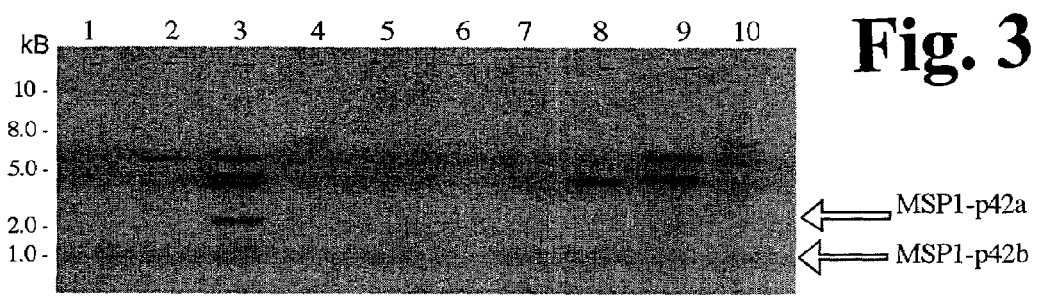
FIGS. 3A–B show analysis of MSP1.42 gene DNA integration and transcription in plants transformed with MSP1.42FUPa and MSP12.42FUPb expression constructs. 32[P]-labeled MSP1.42 FUP was used as the hybridization probe for these blots. (A) Southern blot of wild type plants digested with Bam HI (lane 1) or with Sac1 (lane 6), MSP1.42FUPa transformants digested with BamHI (lanes 2 and 3) or Sac1 (lanes 7 and 8), and MSP1.42FUPb transformants digested with Bam HI (lanes 4 and 5) and Sac1 (lanes 9 and 10). Arrows indicate the expected fragment sizes for Bam-H1 digests of MSP1.42FUPa (3.0 kB) and MSP1.42FUPb (1.2 kB). (B) Northern blot of wild type plants (lane 6), MSP1.42FUPa transformants (lanes 1–3) and MSP1.42FUPb transformants (lanes 4 and 5). Blots were exposed to X-ray film for one week before developing.
Figure 3B:
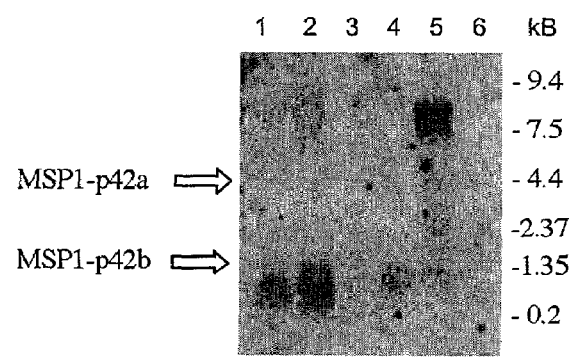

Two constructs utilizing a modified MSP1.42 FUP sequence with higher G:C content resulting in the absence of RNA instability sequences as well as additional modifications to control intracellular localization (NtMSP1.42) were used to generate a third series of transformed plants. For the NtMSP1.42C construct (FIG. 2), plant expression was targeted to the cytoplasm. For the NtMSP1.42S construct (FIG. 2), the sequence was optimized for plant expression and targeting of the expressed protein to the endoplasmic reticulum and for extracellular secretion.

Figure 5A:
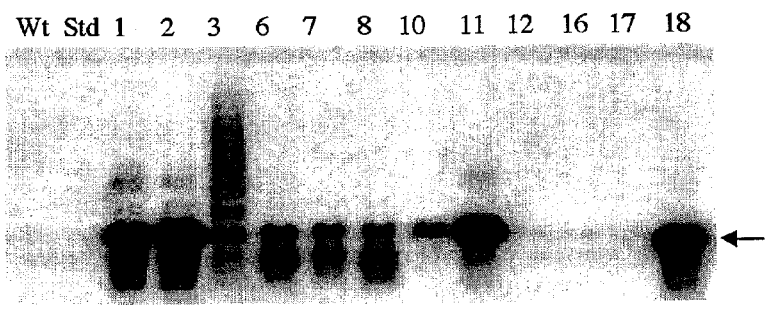
FIGS. 5A–B show analysis of MSP1.42 gene transcription in plants transformed with NtMSP1.42C constructs (5A, lanes 1–12) and NtMSP1.42S constructs (5B, lanes 1–12). Results for wild type RNA are indicated as the "Wt" lane. 32[P]-NtMSP1.42C was used as the hybridization probe.
Figure 5B:
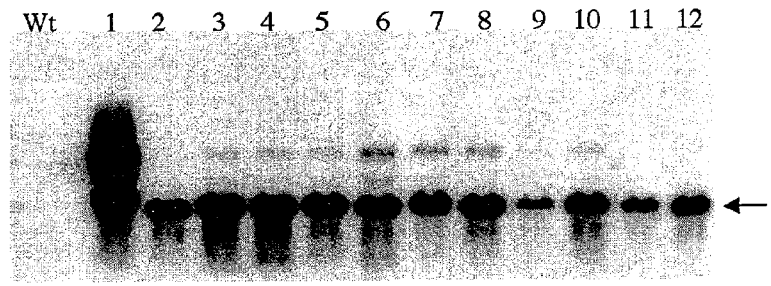

In the case of plants transformed with both NtMSP1.42C (FIG. 5A) and NtMSP1.42S (FIG. 5B) constructs, Northern blot analyses using the NtMSP1.42C gene as a probe consistently identified full-length, hybridizing bands of approximately 1.2 kB, after a 6 hour exposure of blots. Based on the variable intensity of the hybridizing bands, individual plants appeared to differ in transcription levels in this experiment. Generally, mRNA levels were higher for NtMSP1.42S transgenic plants than for NtMSP1.42C, plants whose signals were highly variable in intensity. Wild-type tobacco plant RNA did not show any hybridization with this probe.

Protein Analysis from NtMSP1.42 Constructs

Figure 6A:
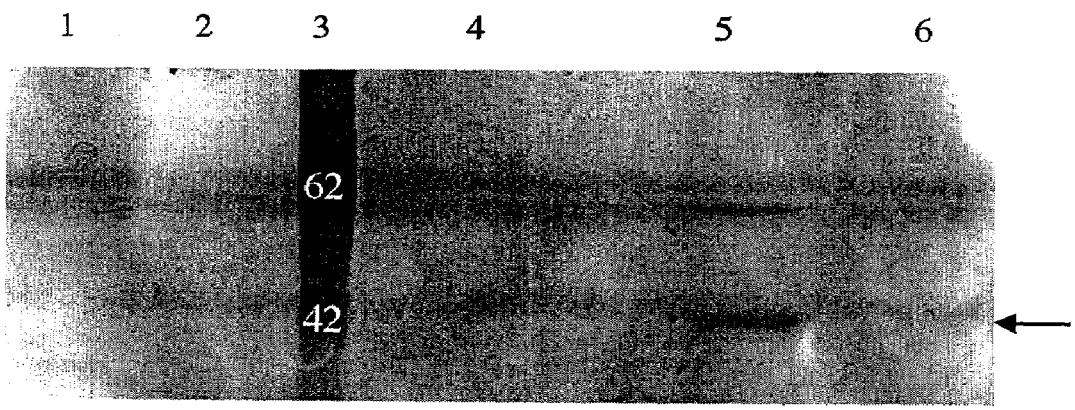
FIGS. 6A–B shows immunological analysis of protein produced by tobacco plants transformed with NtMSP1.42C and NtMSP1.42S constructs. MAb 5.2 antibodies were used as the primary antibody. Rabbit anti-mouse was the secondary and alkaline phosphotase labeled goat anti-rabbit was the third antibody. Benchmark molecular weight standards were run in lane 3; positions of 42 and 62 kDa bands are indicated. Arrows indicate the position of the expected 42 kDa protein. (A) Western blot of proteins extracted from a wild type plant (lane 1) and NtMSP1.42C transformants (lanes 4–6). (B) Western blot of a baculovirus-expressed MSP1.42FUP protein (lane 1), Benchmark molecular weight standards (lane 2) and NtMSP1.42S transformants (lanes 3–8).
Figure 6B:
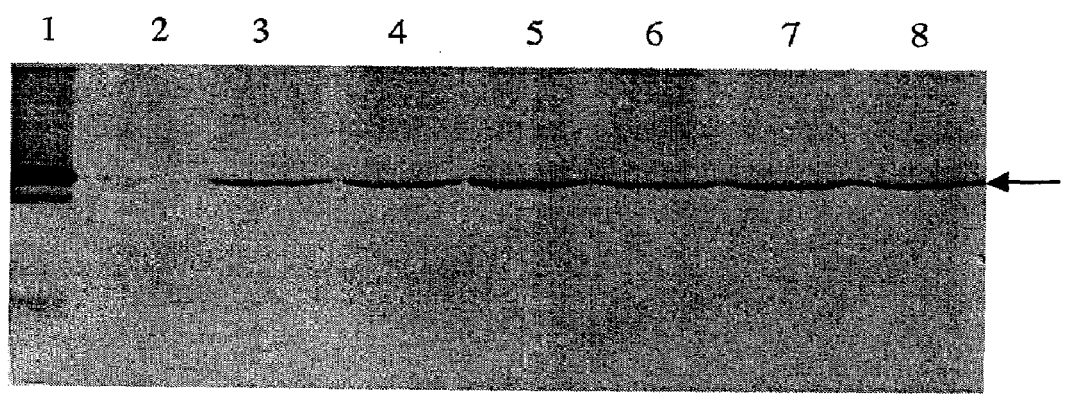

Western blots using monoclonal or polyclonal antibodies specific for parasite MSP-1 p42 resulted in visible bands in NtMSP1.42 transgenic plants. The plants containing the NtMSP1.42 constructs were positive by immunoblot using a MSP-1-specific monoclonal antibody (MAb 5.2). Three NtMSP1.42C plants positive on Northern blot were tested by western blot. MAb 5.2-reactive proteins were detected in some, but not all, of the NtMSP1.42C transgenic plants (FIG. 6A). The band intensities for these samples were faint and required a 1 hour developing time. NtMSP1.42S (FIG. 6B) transgenic plants were chosen for protein studies by the order of when they rooted, irrespective of their Northern blot result. In contrast to NtMSP1.42C plants, all NTMSP1.42S plant samples produced intense immunoblot bands of the appropriate size. Using MSP1.42 FUP protein expressed in baculovirus as a positive control in these immunoblots, the molecular sizes of recombinant NtMSP1.42C and NtMSP1.42S polypeptides produced by these transgenic tobacco plants were similar in size to baculovirus MSP1.42. Wild type plants either did not react or reacted non-specifically, producing a faint band at about 25 kD, but no 42 kD band was visible.

Discussion

To eliminate the potential problematic sequences of the MSP1.42 FUP and FVO genes (e.g., Examples 1 and 2), a synthetic FUP MSP1.42 sequence (NtMSP1.42) having a modified codon preference and lower A:T content (56% ) was used to generate another series of constructs. The A:T content of NtMSP1.42 was closer to that of the consensus codon usage for tobacco and the NtMSP1.42 sequence contained no potential poly-adenylation sequences, cryptic intron splice sites and only one ATTTA RNA instability sequence, which was removed prior to tobacco transformation. Two different constructs using NtMSP1.42 were created: the first contained an upstream signal sequence and 3' ER retention signal and was targeted for secretion (NtMSP1.42S) and the second contained only the ER retention signal and thus would be retained in the cytoplasm (NtMSP1.42C). RNA preparations of transgenic plants that contained either NtMSP1.42S or NtMSP1.42C contained hybridizing bands of the expected size for intact MSP1.42 mRNA and, in some cases, additional larger sized RNA species. More NtMSP1.42S than NtMSP1.42C plants contained specific transcripts. Transgenic plants containing both constructs were positive by Western blot for the 42 kD MSP1.42 protein. Expression levels were consistently higher in plants containing the secretory, MSP1.42S construct than in transgenic plants containing the cytoplasmic, NtMSP1.42C construct.

Production and stability of *P. falciparum* MSP1.42 RNA transcripts appeared to be major limiting factors for protein expression in tobacco. Exclusion of RNA instability sequences appeared to be essential for the detection of full-length mRNA transcripts. Other interfering sequences, such as the cryptic intron splice sites and premature poly-adenylation signals, also may have contributed to the difficulty in obtaining MSP1.42 gene expression in transgenic plants. Since RNA transcription appeared to be comparable for individual MSP1.42S and MSP1.42C plants that differed in the level of protein expression, protein translation and/or stability may be another limiting factor controlling MSP1.42 production in tobacco. Without being bound by theory, one possibility is that proteins produced through the secretory pathway were more stable than cytoplasmically targeted MSP1.42. MSP1.42C may have been degraded in the acidic, protease filled cytoplasmic environment. In contrast, MSP1.42S produced through the secretory pathway may have been protected from degradation, perhaps through retention in the ER and associated secretory vacuoles. Follow-up studies are planned to determine the intracellular localization of MSP1.42 in transgenic plants expressing the secretory versus cytoplasmic constructs. Since considerable modification of the original *P. falciparum* gene was required to achieve RNA transcription and protein production, these studies have identified key structural elements which appear to regulate foreign gene expression in Planta.

The plant-derived MSP1.42 reacted with a monoclonal antibody specific for a disulfide-dependent, conformational determinant of the native protein (Siddiqui et al. 1987. Proc. Natl. Acad. Sci. USA 84:3014). This indicated that, not only was the protein expressed, but it also was folded correctly. Since MSP1.42 protein now has been expressed in a stable form in plants, a number of additional studies may be performed to establish the feasibility of large-scale transgenic plant production of this candidate malaria vaccine antigen. First, protein concentrations may be assessed for specific plant tissue (e.g., roots, stems, and leaves) to determine the yield and tissue distribution of plant-derived MSP1.42. In addition, cells from tissue with the highest expression levels may be cultured in suspension to evaluate protein compartmentalization. Thirdly, NtMSP1.42S protein purified by immunoaffinity chromatography may be evaluated for its physical properties including its molecular size, type and extent of glycosylation, and molecular heterogeneity. Finally, the immunogenicity of purified NtMSP1.42 may be evaluated and compared to that of baculovirus MSP1.42 (Chang et al. 1996. Infect Immun 64(1):253). It has recently been reported MSP1.42 produced in transgenic mice differs immunologically from baculovirus MSP1.42 due primarily to the differing nature of glycosylation patterns (Stowers et al. 2002. Proc Natl Acad Sci USA 99(1): 339).

Production levels of NtMSP1.42 may be enhanced by optimization of the expression construct. For example, use of the double CaMV35S promoter construct and the AMV enhancer resulted in significantly higher transcription and translation of foreign proteins in plants (Datla et al. 1993. Plant Science 94:139) than the single CaMV35S expression cassettes used in the current study. It may also be desirable to remove the ER retention signal since this has resulted in higher secretion levels for certain foreign proteins in plants.

In the present invention, the entire 42 kDa NtMSP1.42S coding region has been integrated into the tobacco plant genome and the complete gene has been stably expressed. MSP1.42S-producing transgenic plants may serve as a reliable source of raw material to economically produce malaria vaccine protein in an animal protein-free system.

"Sequence Listing".

We claim:

1. An isolated p42 nucleic acid encoding a p42 polypeptide from the C-terminal processing fragment of *Plasmodium falciparum* major merozoite surface protein gp195, wherein said isolated p42 nucleic acid comprises a nucleic acid sequence having at least 95% sequence identity to the nucleic acid sequence of SEQ ID NO: 1 or SEQ ID NO: 3.

2. The nucleic acid of claim 1, wherein said isolated p42 nucleic acid has enhanced RNA transcription and stability in a tobacco plant host cell.

3. The isolated p42 nucleic acid of claim 1 comprising the nucleic acid sequence of SEQ ID NO: 1 or SEQ ID NO: 3.

4. An *Agrobacterium*-mediated plant expression system for the production of a p42 polypeptide from the C-terminal processing fragment of *Plasmodium falciparum* major merozoite surface protein gp195, said system comprising a DNA construct consisting of operatively linked nucleic acid encoding a modified T-region but no vir-region, wherein said modified T-region comprises naturally occurring border sequences consisting of about 23 nucleotides at the extremities of said modified T-region and wherein said modified T-region further comprises a nucleic acid sequence having at least 95% sequence identity to the nucleic acid sequence of SEQ ID NO: 1 or SEQ ID NO: 3.

5. A method for production of a p42 polypeptide, comprising the steps of:

(a) introducing an *Agrobacterium* strain into a plant cell wherein said *Agrobacterium* strain comprises at least one plasmid comprising the vir-region of a tumor-inducing plasmid but having no T-region, and at least one other plasmid comprising the modified T-region of claim 4 but having no vir-region, wherein said plant cell becomes transformed; and (b) extracting said p42 polypeptide from said transformed plant cell.

6. The method of claim 5 wherein said *Agrobacterium* strain is *Agrobacterium tumefaciens* strain LBA4404.

7. The isolated p42 nucleic acid of claim 1 wherein the nucleic acid consists of a nucleic acid sequence with at least 95% sequence identity to the nucleic acid sequence of SEQ ID NO: 1 or SEQ ID NO: 3.

8. The *Agrobacterium*-mediated plant expression system of claim 5, wherein the modified T-region comprises the nucleic acid sequence of SEQ ID NO: 1 or SEQ ID NO: 3.

9. The *Agrobacterium*-mediated plant expression system of claim 4, wherein the modified T-region consists of a nucleic acid sequence with at least 95% sequence identity to the nucleic acid sequence of, SEQ ID NO: 1 or SEQ ID NO: 3.

10. The isolated p42 nucleic acid of claim 1, wherein said nucleic acid comprises a nucleic acid sequence having at least 98% sequence identity to the nucleic acid sequence of SEQ ID NO: 1 or SEQ ID NO: 3.

11. The isolated p42 nucleic acid of claim 10 wherein the nucleic acid consists of a nucleic acid sequence with at least 98% sequence identity to the nucleic acid sequence of SEQ ID NO: 1 or SEQ ID NO: 3.

12. The isolated p42 nucleic acid of claim 11 consists of the nucleic acid sequence of SEQ ID NO: 1 or SEQ ID NO: 3.

13. The *Agrobacterium*-mediated plant expression system of claim 4, wherein the modified T-region comprises a nucleic acid sequence having at least 98% sequence identity to the nucleic acid sequence of SEQ ID NO: 1 or SEQ ID NO: 3.

14. The *Agrobacterium*-mediated plant expression system of claim 13, wherein the modified T-region consists of a nucleic acid sequence with at least 98% sequence identity to the nucleic acid sequence of SEQ ID NO: 1 or SEQ ID NO: 3.

15. The *Agrobacterium*-mediated plant expression system of claim 14, wherein the nucleic acid sequence of the modified T-region is SEQ ID NO: 1 or SEQ ID NO: 3.

* * * * *

SEQUENCE LISTING

```
<160> NUMBER OF SEQ ID NOS: 19

<210> SEQ ID NO 1
<211> LENGTH: 1149
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(24)
<223> OTHER INFORMATION:

<400> SEQUENCE: 1
gccgaattcg acaacatcct cagtgacaac atcctcagtg gcttcgagaa cgagtacgac        60
gtaatctacc taaagcccct tgccggtgtc taccgttcat tgaagaaaca gatagaaaag       120
aatattttca cgttcaacct caacctaaat gacatcctca actcgcgcct caagaagcga       180
aaatacttcc tcgacgtgtt ggaatccgac cttatgcaat tcaagcacat tagctctaac       240
gagtacatca tagaggacag cttcaagctc ttgaattcag aacagaagaa caccctccta       300
aagtcctaca aatacattaa ggagtctgtt gagaacgaca tcaagttcgc ccaggaagga       360
attagctact atgagaaagt cctggctaaa tacaaggacg acttggaaag cattaagaag       420
gtaatcaaag aagagaagga aaagtttccg agctctccac ccacaactcc cccatcgcct       480
gcaaagaccg acgagcagaa aaagagaagt aagttccttc cattcctcac caacatcgaa       540
actctatata caacctggt gaacaagatt gatgactact taatcaactt gaaggcgaaa       600
attaatgact gtaacgtcga aaaggatgaa gcccacgtta agatcaccaa gctttccgat       660
ctcaaagcca tcgacgataa gattgacctg tttaagaacc acaacgattt cgacgcaatc       720
aaaaagttga tcaacgacga tactaagaaa gacatgcttg gaaaactgct gtcgacaggc       780
ttggtccaaa acttcccgaa caccattata agcaagctga tcgaaggaaa gtttcaggat       840
atgctgaaca tctctcagca tcaatgcgtg aagaagcaat gtcccgagaa ttcaggttgc       900
ttccgccact tagacgaaag ggaggaatgt aaatgcctgc tgaattataa acaggaagga       960
```

```
gacaagtgcg tagagaatcc taacccaacc tgtaacgaaa ataacggtgg ctgcgatgct    1020
gacgctaagt gtaccgagga ggacagcggt tccaatggca agaaaataac ttgcgaatgc    1080
acgaagcccg atagttaccc tctcttcgac ggtatcttct gctcccatga tgagctttaa    1140
gagctcacc                                                           1149
```

<210> SEQ ID NO 2
<211> LENGTH: 383
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (380)..(380)
<223> OTHER INFORMATION: "Xaa" at position 380 represents a stop codon

<400> SEQUENCE: 2

```
Ala Glu Phe Asp Asn Ile Leu Ser Asp Asn Ile Leu Ser Gly Phe Glu
1               5                   10                  15

Asn Glu Tyr Asp Val Ile Tyr Leu Lys Pro Leu Ala Gly Val Tyr Arg
            20                  25                  30

Ser Leu Lys Lys Gln Ile Glu Lys Asn Ile Phe Thr Phe Asn Leu Asn
        35                  40                  45

Leu Asn Asp Ile Leu Asn Ser Arg Leu Lys Lys Arg Lys Tyr Phe Leu
    50                  55                  60

Asp Val Leu Glu Ser Asp Leu Met Gln Phe Lys His Ile Ser Ser Asn
65                  70                  75                  80

Glu Tyr Ile Ile Glu Asp Ser Phe Lys Leu Leu Asn Ser Glu Gln Lys
                85                  90                  95

Asn Thr Leu Leu Lys Ser Tyr Lys Tyr Ile Lys Glu Ser Val Glu Asn
            100                 105                 110

Asp Ile Lys Phe Ala Gln Glu Gly Ile Ser Tyr Tyr Glu Lys Val Leu
        115                 120                 125

Ala Lys Tyr Lys Asp Asp Leu Glu Ser Ile Lys Lys Val Ile Lys Glu
    130                 135                 140

Glu Lys Glu Lys Phe Pro Ser Ser Pro Thr Thr Pro Pro Ser Pro
145                 150                 155                 160

Ala Lys Thr Asp Glu Gln Lys Lys Glu Ser Lys Phe Leu Pro Phe Leu
                165                 170                 175

Thr Asn Ile Glu Thr Leu Tyr Asn Asn Leu Val Asn Lys Ile Asp Asp
            180                 185                 190

Tyr Leu Ile Asn Leu Lys Ala Lys Ile Asn Asp Cys Asn Val Glu Lys
        195                 200                 205

Asp Glu Ala His Val Lys Ile Thr Lys Leu Ser Asp Leu Lys Ala Ile
    210                 215                 220

Asp Asp Lys Ile Asp Leu Phe Lys Asn His Asn Asp Phe Asp Ala Ile
225                 230                 235                 240

Lys Lys Leu Ile Asn Asp Asp Thr Lys Lys Asp Met Leu Gly Lys Leu
                245                 250                 255

Leu Ser Thr Gly Leu Val Gln Asn Phe Pro Asn Thr Ile Ile Ser Lys
            260                 265                 270

Leu Ile Glu Gly Lys Phe Gln Asp Met Leu Asn Ile Ser Gln His Gln
        275                 280                 285

Cys Val Lys Lys Gln Cys Pro Glu Asn Ser Gly Cys Phe Arg His Leu
    290                 295                 300
```

```
Asp Glu Arg Glu Glu Cys Lys Cys Leu Leu Asn Tyr Lys Gln Glu Gly
305                 310                 315                 320

Asp Lys Cys Val Glu Asn Pro Asn Pro Thr Cys Asn Glu Asn Asn Gly
            325                 330                 335

Gly Cys Asp Ala Asp Ala Lys Cys Thr Glu Glu Asp Ser Gly Ser Asn
        340                 345                 350

Gly Lys Lys Ile Thr Cys Glu Cys Thr Lys Pro Asp Ser Tyr Pro Leu
    355                 360                 365

Phe Asp Gly Ile Phe Cys Ser His Asp Glu Leu Xaa Glu Leu Thr
    370                 375                 380
```

<210> SEQ ID NO 3
<211> LENGTH: 1149
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(24)
<223> OTHER INFORMATION:

<400> SEQUENCE: 3

```
cggatccaag gagatataac aatggacaac atcctcagtg gcttcgagaa cgagtacgac    60
gtaatctacc taaagcccct tgccggtgtc taccgttcat tgaagaaaca gatagaaaag   120
aatattttca cgttcaacct caacctaaat gacatcctca actcgcgcct caagaagcga   180
aaatacttcc tcgacgtgtt ggaatccgac cttatgcaat tcaagcacat tagctctaac   240
gagtacatca tagaggacag cttcaagctc ttgaattcag aacagaagaa caccctccta   300
aagtcctaca aatacattaa ggagtctgtt gagaacgaca tcaagttcgc ccaggaagga   360
attagctact atgagaaagt cctggctaaa tacaaggacg acttggaaag cattaagaag   420
gtaatcaaag aagagaagga aaagtttccg agctctccac ccacaactcc cccatcgcct   480
gcaaagaccg acgagcagaa aaagaaagt aagttccttc cattcctcac caacatcgaa   540
actctatata caacctggt gaacaagatt gatgactact aatcaactt gaaggcgaaa   600
attaatgact gtaacgtcga aaaggatgaa gcccacgtta agatcaccaa gctttccgat   660
ctcaaagcca tcgacgataa gattgacctg tttaagaacc acaacgattt cgacgcaatc   720
aaaaagttga tcaacgacga tactaagaaa gacatgcttg gaaaactgct gtcgacaggc   780
ttggtccaaa acttcccgaa caccattata agcaagctga tcgaaggaaa gtttcaggat   840
atgctgaaca tctctcagca tcaatgcgtg aagaagcaat gtcccgagaa ttcaggttgc   900
ttccgccact tagacgaaag ggaggaatgt aaatgcctgc tgaattataa acaggaagga   960
gacaagtgcg tagagaatcc taacccaacc tgtaacgaaa ataacggtgg ctgcgatgct  1020
gacgctaagt gtaccgagga ggacagcggt tccaatggca gaaaataac ttgcgaatgc  1080
acgaagcccg atagttaccc tctcttcgac ggtatcttct gctcccatga tgagctttaa  1140
gagctcacc                                                          1149
```

<210> SEQ ID NO 4
<211> LENGTH: 383
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (380)..(380)
<223> OTHER INFORMATION: "Xaa" at position 380 represents a stop codon

<400> SEQUENCE: 4

Arg Ile Gln Gly Asp Ile Thr Met Asp Asn Ile Leu Ser Gly Phe Glu
1               5                   10                  15

Asn Glu Tyr Asp Val Ile Tyr Leu Lys Pro Leu Ala Gly Val Tyr Arg
            20                  25                  30

Ser Leu Lys Lys Gln Ile Glu Lys Asn Ile Phe Thr Phe Asn Leu Asn
        35                  40                  45

Leu Asn Asp Ile Leu Asn Ser Arg Leu Lys Lys Arg Lys Tyr Phe Leu
50                  55                  60

Asp Val Leu Glu Ser Asp Leu Met Gln Phe Lys His Ile Ser Ser Asn
65                  70                  75                  80

Glu Tyr Ile Ile Glu Asp Ser Phe Lys Leu Leu Asn Ser Glu Gln Lys
                85                  90                  95

Asn Thr Leu Leu Lys Ser Tyr Lys Tyr Ile Lys Glu Ser Val Glu Asn
            100                 105                 110

Asp Ile Lys Phe Ala Gln Glu Gly Ile Ser Tyr Tyr Glu Lys Val Leu
        115                 120                 125

Ala Lys Tyr Lys Asp Asp Leu Glu Ser Ile Lys Lys Val Ile Lys Glu
130                 135                 140

Glu Lys Glu Lys Phe Pro Ser Ser Pro Pro Thr Thr Pro Ser Pro
145                 150                 155                 160

Ala Lys Thr Asp Glu Gln Lys Lys Glu Ser Lys Phe Leu Pro Phe Leu
            165                 170                 175

Thr Asn Ile Glu Thr Leu Tyr Asn Asn Leu Val Asn Lys Ile Asp Asp
        180                 185                 190

Tyr Leu Ile Asn Leu Lys Ala Lys Ile Asn Asp Cys Asn Val Glu Lys
        195                 200                 205

Asp Glu Ala His Val Lys Ile Thr Lys Leu Ser Asp Leu Lys Ala Ile
210                 215                 220

Asp Asp Lys Ile Asp Leu Phe Lys Asn His Asn Asp Phe Asp Ala Ile
225                 230                 235                 240

Lys Lys Leu Ile Asn Asp Asp Thr Lys Lys Asp Met Leu Gly Lys Leu
            245                 250                 255

Leu Ser Thr Gly Leu Val Gln Asn Phe Pro Asn Thr Ile Ile Ser Lys
        260                 265                 270

Leu Ile Glu Gly Lys Phe Gln Asp Met Leu Asn Ile Ser Gln His Gln
        275                 280                 285

Cys Val Lys Lys Gln Cys Pro Glu Asn Ser Gly Cys Phe Arg His Leu
290                 295                 300

Asp Glu Arg Glu Glu Cys Lys Cys Leu Leu Asn Tyr Lys Gln Glu Gly
305                 310                 315                 320

Asp Lys Cys Val Glu Asn Pro Asn Pro Thr Cys Asn Glu Asn Asn Gly
            325                 330                 335

Gly Cys Asp Ala Asp Ala Lys Cys Thr Glu Glu Asp Ser Gly Ser Asn
        340                 345                 350

Gly Lys Lys Ile Thr Cys Glu Cys Thr Lys Pro Asp Ser Tyr Pro Leu
        355                 360                 365

Phe Asp Gly Ile Phe Cys Ser His Asp Glu Leu Xaa Glu Leu Thr
370                 375                 380

<210> SEQ ID NO 5

<211> LENGTH: 38
<212> TYPE: DNA
<213> ORGANISM: Artificial sequence
<220> FEATURE:
<223> OTHER INFORMATION: synthetic

<400> SEQUENCE: 5
cgggatccca aggagatacc atggcagtaa ctccttcc                              38

<210> SEQ ID NO 6
<211> LENGTH: 42
<212> TYPE: DNA
<213> ORGANISM: Artificial sequence
<220> FEATURE:
<223> OTHER INFORMATION: synthetic

<400> SEQUENCE: 6
ctgcgagctc ttattaaagc tcatcatgct gcagaaaata cc                         42

<210> SEQ ID NO 7
<211> LENGTH: 28
<212> TYPE: DNA
<213> ORGANISM: Artificial sequence
<220> FEATURE:
<223> OTHER INFORMATION: synthetic

<400> SEQUENCE: 7
ctgcgagctc ttattaatga tgatgatg                                         28

<210> SEQ ID NO 8
<211> LENGTH: 42
<212> TYPE: DNA
<213> ORGANISM: Artificial sequence
<220> FEATURE:
<223> OTHER INFORMATION: synthetic

<400> SEQUENCE: 8
ggtgagctct taaagctcat catgggagca gaagataccg tc                         42

<210> SEQ ID NO 9
<211> LENGTH: 24
<212> TYPE: DNA
<213> ORGANISM: Artificial sequence
<220> FEATURE:
<223> OTHER INFORMATION: synthetic

<400> SEQUENCE: 9
gccgaattcg acaacatcct cagt                                             24

<210> SEQ ID NO 10
<211> LENGTH: 42
<212> TYPE: DNA
<213> ORGANISM: Artificial sequence
<220> FEATURE:
<223> OTHER INFORMATION: synthetic

<400> SEQUENCE: 10
ggtgagctct taaagctcat catgggagca gaagataccg tc                         42

<210> SEQ ID NO 11
<211> LENGTH: 30
<212> TYPE: DNA
<213> ORGANISM: Artificial sequence
<220> FEATURE:
<223> OTHER INFORMATION: synthetic

<400> SEQUENCE: 11
agagctaatg tgcttgaatt gcataaggtc         30

<210> SEQ ID NO 12
<211> LENGTH: 30
<212> TYPE: DNA
<213> ORGANISM: Artificial sequence
<220> FEATURE:
<223> OTHER INFORMATION: synthetic

<400> SEQUENCE: 12
gaccttatgc aattcaagca cattagctct         30

<210> SEQ ID NO 13
<211> LENGTH: 1235
<212> TYPE: DNA
<213> ORGANISM: Artificial sequence
<220> FEATURE:
<223> OTHER INFORMATION: synthetic

<400> SEQUENCE: 13
attggatcca ctaaaatgtg gtcttggaag tgtcttttat tctgggctgt cttggtgacc     60
gccactcttt gcacagcagc gatctctgtt actatggaca catcctcag tggcttcgag    120
aacgagtacg acgtaatcta cctaaagccc cttgccggtg tctaccgttc attgaagaaa    180
cagatagaaa agaatatttt cacgttcaac ctcaacctaa atgacatcct caactcgcgc    240
ctcaagaagc gaaatacttt cctcgacgtg ttggaatccg accttatgca atttaagcac    300
attagctcta acgagtacat catagaggac agcttcaagc tcttgaattc agaacagaag    360
aacaccctcc taaagtccta caaatacatt aaggagtctg ttgagaacga catcaagttc    420
gcccaggaag gaattagcta ctatgagaaa gtcctggcta atacaaagga cgacttggaa    480
agcattaaga aggtaatcaa agaagagaag gaaaagtttc cgagctctcc acccacaact    540
cccccatcgc ctgcaaagac cgacgagcag aaaaaagaaa gtaagttcct tccattcctc    600
accaacatcg aaactctata taacaacctg gtgaacaaga ttgatgacta cttaatcaac    660
ttgaaggcga aaattaatga ctgtaacgtc gaaaaggatg aagcccacgt taagatcacc    720
aagctttccg atctcaaagc catcgacgat aagattgacc tgtttaagaa ccacaacgat    780
ttcgacgcaa tcaaaaagtt gatcaacgac gatactaaga agacatgct tggaaaactg    840
ctgtcgacag gcttggtcca aaacttcccg aacaccatta agcaagct gatcgaagga     900
aagtttcagg atatgctgaa catctctcag catcaatgcg tgaagaagca atgtcccgag    960
aattcaggtt gcttccgcca cttagacgaa agggaggaat gtaaatgcct gctgaattat    1020
aaacaggaag agacaagtg cgtagagaat cctaacccaa cctgtaacga aaataacggt    1080
ggctgcgatg ctgacgctaa gtgtaccgag gaggacagcg gttccaatgg caagaaaata    1140
acttgcgaat gcacgaagcc cgatagttac cctctcttcg acggtatctt ctgctcccca    1200
cctcatcatc atcatcatca ttaataaggt accta        1235

<210> SEQ ID NO 14
<211> LENGTH: 402
<212> TYPE: PRT
<213> ORGANISM: Artificial sequence
<220> FEATURE:
<223> OTHER INFORMATION: synthetic

<400> SEQUENCE: 14

Met Trp Ser Trp Lys Cys Leu Leu Phe Trp Ala Val Leu Val Thr Ala
1               5                   10                  15

Thr Leu Cys Thr Ala Ala Ile Ser Val Thr Met Asp Asn Ile Leu Ser
            20                  25                  30

Gly Phe Glu Asn Glu Tyr Asp Val Ile Tyr Leu Lys Pro Leu Ala Gly
            35                  40                  45

Val Tyr Arg Ser Leu Lys Lys Gln Ile Glu Lys Asn Ile Phe Thr Phe
        50                  55                  60

Asn Leu Asn Leu Asn Asp Ile Leu Asn Ser Arg Leu Lys Lys Arg Lys
65                  70                  75                  80

Tyr Phe Leu Asp Val Leu Glu Ser Asp Leu Met Gln Phe Lys His Ile
                85                  90                  95

Ser Ser Asn Glu Tyr Ile Ile Glu Asp Ser Phe Lys Leu Leu Asn Ser
            100                 105                 110

Glu Gln Lys Asn Thr Leu Leu Lys Ser Tyr Lys Tyr Ile Lys Glu Ser
            115                 120                 125

Val Glu Asn Asp Ile Lys Phe Ala Gln Glu Gly Ile Ser Tyr Tyr Glu
        130                 135                 140

Lys Val Leu Ala Lys Tyr Lys Asp Asp Leu Glu Ser Ile Lys Lys Val
145                 150                 155                 160

Ile Lys Glu Glu Lys Glu Lys Phe Pro Ser Ser Pro Thr Thr Pro
                165                 170                 175

Pro Ser Pro Ala Lys Thr Asp Glu Gln Lys Lys Glu Ser Lys Phe Leu
            180                 185                 190

Pro Phe Leu Thr Asn Ile Glu Thr Leu Tyr Asn Asn Leu Val Asn Lys
            195                 200                 205

Ile Asp Asp Tyr Leu Ile Asn Leu Lys Ala Lys Ile Asn Asp Cys Asn
        210                 215                 220

Val Glu Lys Asp Glu Ala His Val Lys Ile Thr Lys Leu Ser Asp Leu
225                 230                 235                 240

Lys Ala Ile Asp Asp Lys Ile Asp Leu Phe Lys Asn His Asn Asp Phe
                245                 250                 255

Asp Ala Ile Lys Lys Leu Ile Asn Asp Asp Thr Lys Lys Asp Met Leu
            260                 265                 270

Gly Lys Leu Leu Ser Thr Gly Leu Val Gln Asn Phe Pro Asn Thr Ile
            275                 280                 285

Ile Ser Lys Leu Ile Glu Gly Lys Phe Gln Asp Met Leu Asn Ile Ser
        290                 295                 300

Gln His Gln Cys Val Lys Lys Gln Cys Pro Glu Asn Ser Gly Cys Phe
305                 310                 315                 320

Arg His Leu Asp Glu Arg Glu Glu Cys Lys Cys Leu Leu Asn Tyr Lys
                325                 330                 335

Gln Glu Gly Asp Lys Cys Val Glu Asn Pro Asn Pro Thr Cys Asn Glu
            340                 345                 350

Asn Asn Gly Gly Cys Asp Ala Asp Ala Lys Cys Thr Glu Glu Asp Ser
            355                 360                 365

Gly Ser Asn Gly Lys Lys Ile Thr Cys Glu Cys Thr Lys Pro Asp Ser
        370                 375                 380

Tyr Pro Leu Phe Asp Gly Ile Phe Cys Ser Pro His His His
385                 390                 395                 400

His His

<210> SEQ ID NO 15
<211> LENGTH: 150
<212> TYPE: DNA

<213> ORGANISM: Artificial sequence
<220> FEATURE:
<223> OTHER INFORMATION: synthetic

<400> SEQUENCE: 15

```
aaaatgatat taaatttgca caggaaggta taagttatta tgaaaaggtt aacattgaga      60
ccttatacaa taacttagtt aataaaattg acgattactt tccagaaaat tctggatgtt     120
tcagacattt agatgaaaga gaagaatgta                                      150
```

<210> SEQ ID NO 16
<211> LENGTH: 142
<212> TYPE: DNA
<213> ORGANISM: Artificial sequence
<220> FEATURE:
<223> OTHER INFORMATION: synthetic

<400> SEQUENCE: 16

```
aatttcaaaa tgttttagaa tcagatttaa ttccatataa agatttaaca tcaagtaatt      60
atgttgtcaa agatccatat aaatttctta ataaagaaaa aagagataaa ttcttaagca     120
gttataatta tattaaggat tc                                              142
```

<210> SEQ ID NO 17
<211> LENGTH: 5
<212> TYPE: PRT
<213> ORGANISM: Artificial sequence
<220> FEATURE:
<223> OTHER INFORMATION: linker consensus sequence

<400> SEQUENCE: 17

Gly Ser Gly Gly Ser
1               5

<210> SEQ ID NO 18
<211> LENGTH: 4
<212> TYPE: DNA
<213> ORGANISM: Artificial sequence
<220> FEATURE:
<223> OTHER INFORMATION: linker consensus sequence

<400> SEQUENCE: 18 gggs                                                                    4

<210> SEQ ID NO 19
<211> LENGTH: 4
<212> TYPE: PRT
<213> ORGANISM: Artificial sequence
<220> FEATURE:
<223> OTHER INFORMATION: endoplasmic reticulum retention signal

<400> SEQUENCE: 19

His Asp Glu Leu
1